United States Patent
Shoenfeld et al.

(10) Patent No.: US 9,987,372 B2
(45) Date of Patent: Jun. 5, 2018

(54) PHOSPHORYLCHOLINE CONJUGATES AND USES THEREOF

(71) Applicant: TPCERA LTD., Jerusalem (IL)

(72) Inventors: Yehuda Shoenfeld, Ramat Gan (IL); Miriam Blank, Tel Aviv (IL)

(73) Assignee: TPCERA LTD., Jerusalem (IL)

( * ) Notice: Subject to any disclaimer, the term of this patent is extended or adjusted under 35 U.S.C. 154(b) by 0 days. days.

(21) Appl. No.: 14/766,108

(22) PCT Filed: Feb. 5, 2014

(86) PCT No.: PCT/IL2014/050124
§ 371 (c)(1),
(2) Date: Aug. 5, 2015

(87) PCT Pub. No.: WO2014/122646
PCT Pub. Date: Aug. 14, 2014

(65) Prior Publication Data
US 2016/0193350 A1    Jul. 7, 2016

Related U.S. Application Data

(60) Provisional application No. 61/760,668, filed on Feb. 5, 2013.

(51) Int. Cl.
| | |
|---|---|
| *A61K 38/07* | (2006.01) |
| *A61K 47/48* | (2006.01) |
| *A61K 31/66* | (2006.01) |
| *C07F 9/09* | (2006.01) |
| *A61K 31/685* | (2006.01) |
| *A61K 47/54* | (2017.01) |
| *A61K 47/64* | (2017.01) |
| *A61K 47/68* | (2017.01) |

(52) U.S. Cl.
CPC .......... *A61K 47/4833* (2013.01); *A61K 31/66* (2013.01); *A61K 31/685* (2013.01); *A61K 47/54* (2017.08); *A61K 47/549* (2017.08); *A61K 47/646* (2017.08); *A61K 47/6803* (2017.08); *C07F 9/091* (2013.01)

(58) Field of Classification Search
None
See application file for complete search history.

(56) References Cited

U.S. PATENT DOCUMENTS

| | | |
|---|---|---|
| 5,455,032 A | 10/1995 | Kinney |
| 7,067,480 B2 | 6/2006 | Harnett |
| 7,097,824 B2 | 8/2006 | Sharma |
| 8,012,483 B2 | 9/2011 | De Faire |
| 2008/0175852 A1 | 7/2008 | Rezanka |
| 2010/0210567 A1 | 8/2010 | Bevec |
| 2010/0303721 A1 | 12/2010 | Weinstock |
| 2011/0166250 A1 | 7/2011 | Pacetti |

FOREIGN PATENT DOCUMENTS

| | | |
|---|---|---|
| EP | 2258728 | 12/2010 |
| EP | 2260873 | 12/2010 |
| WO | 03024474 | 3/2003 |
| WO | 2005052115 | 6/2005 |
| WO | 2006003518 A2 | 1/2006 |
| WO | 2014122646 A1 | 8/2014 |

OTHER PUBLICATIONS

Rossomando et al. ('Characterization and cAMP inhibition of a lysyl-(N-epsilon-5'-phospho) adenosyl phosphoamidase in Dictyostelium discoideum' International Journal of Biochemistry v18(5) 1986 pp. 481-484).*
Uniprot entry for hemocyanin (retrieved from http://www.uniprot.org/uniprot/Q53IP9 on Sep. 14, 2016, 11 pages).*
Singhal et al. ('Specific interaction of liposomes with PMN leukocytes upon incorporating tuftsin in their bilayers' FEBS Letters v178(1) Dec. 1984 pp. 109-113).*
AOCS lipid library (retrieved from http://lipidlibrary.aocs.org/Primer/content.cfm?ItemNumber=39351 on Mar. 20, 2017, 13 pages).*
Pubchem entry (retrieved from https://pubchem.ncbi.nlm.nih.gov/compound/phosphocholine#section=Top on Mar. 20, 2017, 26 pages).*
Anthony et al., (2007) Protective immune mechanisms in helminth infection. Nat Rev Immunol 7(12): 975-87.
Bhasin et al., (2007) Modulation of microglial/macrophage activation by macrophage inhibitory factor (TKP) or tuftsin (TKPR) attenuates the disease course of experimental autoimmune encephalomyelitis. BMC Immunol 8: 10.
Blank et al., (1999) Prevention of experimental antiphospholipid syndrome and endothelial cell activation by synthetic peptides. Proc Natl Acad Sci U S A 96(9): 5164-8.
Chen et al., (2009) Regulation of dendritic cells and macrophages by an anti-apoptotic cell natural antibody that suppresses TLR responses and inhibits inflammatory arthritis. J Immunol 183(2): 1346-59.
Chilton et al., (2004) Flt3-ligand treatment prevents diabetes in NOD mice. Diabetes 53(8): 1995-2002.
Dagan et al., (1987) Tuftsin and tuftsin conjugates potentiate immunogenic processes: effects and possible mechanisms. J Biol Response Mod 6(6): 625-36.

(Continued)

*Primary Examiner* — Karlheinz R. Skowronek
*Assistant Examiner* — Ronald T Niebauer
(74) *Attorney, Agent, or Firm* — The Roy Gross Law Firm, LLC; Roy Gross

(57) ABSTRACT

The present invention provides phosphorylcholine (PC)-conjugates and pharmaceutical compositions, particularly vaccines comprising same for the prevention or treatment of autoimmune diseases. In particular, the PC-conjugates of the present invention are effective in preventing or treating autoimmune diseases associated with pathological inflammation.

8 Claims, 10 Drawing Sheets

(56) References Cited

OTHER PUBLICATIONS

Elliott and Weinstock (2009) Helminthic therapy: using worms to treat immune-mediated disease. Adv Exp Med Biol 666: 157-66.
Goodridge et al., (2007) Phosphorylcholine mimics the effects of ES-62 on macrophages and dendritic cells. Parasite Immunol 29(3): 127-37.
Harnett and Harnett (2009) Immunomodulatory activity and therapeutic potential of the filarial nematode secreted product, ES-62. Adv Exp Med Biol 666: 88-94.
Harnett et al., (2008) The phosphorycholine moiety of the filarial nematode immunomodulator ES-62 is responsible for its anti-inflammatory action in arthritis. Ann Rheum Dis 67(4): 518-23.
Harnett et al., (2010) The therapeutic potential of the filarial nematode-derived immunodulator, ES-62 in inflammatory disease. Clin Exp Immunol 159(3): 256-67.
Harris and Gause (2011) To B or not to B: B cells and the Th2-type immune response to helminths. Trends Immunol 32(2): 80-8.
Houston et al., (2008) Gene inactivation confirms the identity of enzymes involved in nematode phosphorylcholine-N-glycan synthesis. Mol Biochem Parasitol 157(1): 88-91.
Jackson et al., (2009) Review series on helminths, immune modulation and the hygiene hypothesis: immunity against helminths and immunological phenomena in modern human populations: coevolutionary legacies? Immunology 126(1): 18-27.
Kataoka et al., (2011) The nasal dendritic cell-targeting Flt3 ligand as a safe adjuvant elicits effective protection against fatal pneumococcal pneumonia. Infect Immun 79(7): 2819-28.
Krause et al., (1999) Inhibition of diabetes in NOD mice by idiotypic induction of SLE. J Autoimmun 13(1): 49-55.
Kuijk and van Die (2010) Worms to the rescue: can worm glycans protect from autoimmune diseases? IUBMB Life 62 (4): 303-12.
Liu et al., (2009) Helminth infection can reduce insulitis and type 1 diabetes through CD25- and IL-10-independent mechanisms. Infect Immun 77(12): 5347-58.
Lukas et al., (1984) Stimulating effect of tuftsin and its analogues on the defective monocyte chemotaxis in systemic lupus erythematosus. Immunopharmacology 7(3-4): 171-8.
McInnes et al., (2003) A novel therapeutic approach targeting articular inflammation using the filarial nematode-derived phosphorylcholine-containing glycoprotein ES-62. J Immunol 171(4): 2127-33.
Osada et al., (2010) Schistosoma mansoni infection reduces severity of collagen-induced arthritis via down-regulation of pro-inflammatory mediators. Int J Parasitol 39(4): 457-64.
Pöltl et al., (2007) N-glycans of the porcine nematode parasite *Ascaris suum* are modified with phosphorylcholine and core fucose residues. FEBS J 274(3): 714-26.
Ruyssers et al., (2010) Schistosoma mansoni proteins attenuate gastrointestinal motility disturbances during experimental colitis in mice. World J Gastroenterol 16(6): 703-12.
Sewell et al., (2003) Immunomodulation of experimental autoimmune encephalomyelitis by helminth ova immunization. Int Immunol 15(1): 59-69.
Shaw et al., (2003) The autoreactivity of anti-phosphorylcholine antibodies for atherosclerosis-associated neo-antigens and apoptotic cells. J Immunol 170(12): 6151-7.
Shoenfeld et al., (2002) Efficacy of IVIG affinity-purified anti-double-stranded DNA anti-idiotypic antibodies in the treatment of an experimental murine model of systemic lupus erythematosus. Int Immunol 14(11): 1303-11.
Summers et al., (2005) Trichuris suis therapy for active ulcerative colitis: a randomized controlled trial. Gastroenterology 128(4): 825-32.
Summers et al., (2005) Trichuris suis therapy in Crohn's disease. Gut 54(1): 87-90.
Tanaka et al., (2007) Intranasal immunization with phosphorylcholine induces antigen specific mucosal and systemic immune responses in mice. Vaccine 25(14): 2680-7.
Wilson and Maizels (2004) Regulation of allergy and autoimmunity in helminth infection. Clin Rev Allergy Immunol 26 (1): 35-50.
Gottlieb et al: "Tuftsin analogs for probing its specific receptor site on phagocytic cells", European Journal of Biochemistry, vol. 125, Jul. 1982, pp. 631-638.
Ben-Ami, Shor D., et al. "Phosphorylcholine-tuftsin compound prevents development of dextransulfate-sodium-salt induced murine colitis: implications for the treatment of human inflammatory bowel disease." Journal of autoimmunity 56, Jan. 31, 2015, pp. 111-117.
Bashi, Tomer, et al. "Successful modulation of murine lupus nephritis with tuftsinphosphorylcholine." Journal of autoimmunity 59, May 31, 2015, pp. 1-7.
Bashi, Tomer, et al. "Novel therapeutic compound tuftsin-phosphorylcholine attenuates collagen-induced arthritis." Clinical & Experimental Immunology, Feb. 4, 2016, pp. 19-28.

* cited by examiner

FIG. 3A   FIG. 3B
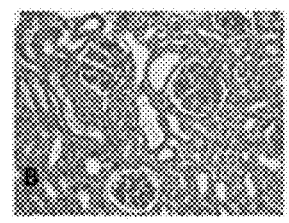
FIG. 4A   FIG. 4B
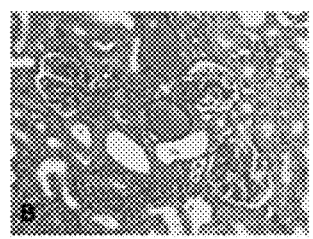
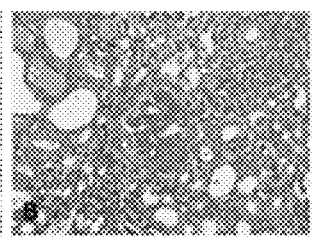
FIG. 5A   FIG. 5B   FIG. 5C

PHOSPHORYLCHOLINE CONJUGATES AND USES THEREOF

This application is a national stage application under 35 U.S.C. § 371 of International Application No. PCT/IL2014/050124, filed Feb. 5, 2014, entitled "Phosphorylcholine Conjugates and Uses Thereof," which claims priority to U.S. Patent Application No. 61/760,668, filed Feb. 5, 2013, the contents of all of which are hereby incorporated herein in their entirety by reference for all purposes.

FIELD OF THE INVENTION

The present invention relates to phosphorylcholine based agents and pharmaceutical compositions comprising same for the prevention and treatment of autoimmune diseases, particularly autoimmune diseases associated with pathological inflammation.

SEQUENCE LISTING

A Sequence Listing submitted in computer readable form (CRF) is hereby incorporated by reference. The CRF file is named Corrected_seq_list_18Nov15_ST25.txt, was created on Nov. 18, 2015, and contains 5 kilobytes.

BACKGROUND OF THE INVENTION

A strong correlation between improved sanitation and significant increase in the prevalence of autoimmune and autoinflammatory syndromes has been demonstrated in western countries. Moreover, a correlation between the presence of parasitic worms (helminths) in certain geographic areas and protection from atopic, autoimmune, and autoinflammatory diseases was reported. These studies led to the "hygiene hypothesis", postulating that the recent increase in autoimmune disease incidences in the west reflects an absence of appropriate priming of the immune response by infectious agents, including parasitic worms, during childhood.

During the last decades many studies reported that infection with parasitic helminthes, or systemic treatment with helminths extracts, can reduce inflammation associated with autoimmune diseases, such as multiple sclerosis (MS), rheumatoid arthritis (RA), type I diabetes mellitus (T1DM), and inflammatory bowel disease (IBD).

Although such studies were successful, using potential pathogens as therapeutic agents has raised ethic and safety issues. Therefore, considerable effort has been spent in identifying and characterizing the parasite-derived molecules responsible for their immunomodulation.

The currently most-well defined nematode-derived immunomodulatory molecule is ES-62. ES-62 is a tetrameric glycoprotein (62 kDa subunits) that has phosphorylcholine (PC)-moieties attached via an N-type glycan.

It has been proposed that the immunomodulatory activity of ES-62 is attributed to the presence of the PC moieties. Further support for the PC immunomodulatory activity was found in other parasitic nematodes like *Ascaris suum* that express only the PC-immunomodulatory moiety.

U.S. Pat. No. 5,455,032 discloses compositions useful for inducing immunoprotection against infections by pathogenic organisms containing phosphocholine antigens, including *Streptococcus pneumoniae* and other microorganisms that have a phosphocholine antigen component on their membranes or capsids. Further disclosed are vaccines and methods for inducing immunoprotection against infection by these pathogenic organisms.

U.S. Pat. No. 7,067,480 discloses the use of a phosphorylcholine-containing glycoprotein, particularly ES-62, in the treatment or prophylaxis of autoimmune diseases associated with abnormal inflammation such as rheumatoid arthritis.

U.S. Pat. No. 8,012,483 discloses a method for identifying subjects at risk of developing ischemic cardiovascular diseases by determining the presence of antibodies, particularly IgM antibodies, toward phosphorylcholine and further discloses pharmaceutical compositions comprising a phosphorylcholine conjugate, or an antibody with specificity to a phosphorylcholine conjugate for active or passive immunogens in the treatment or prevention of atherosclerosis.

U.S. Patent Application, Publication No. 2010/0303721, discloses a method of treating an excessive immune response including an aberrant/enhanced Th1 response with a helminthic parasite preparation. The autoimmune diseases includes Crohn's disease and ulcerative colitis, rheumatoid arthritis, type 1 diabetes mellitus, lupus erythematosus, sarcoidosis, multiple sclerosis, autoimmune thyroiditis, allergic rhinitis, colon polyps/colon cancer and asthma.

There remains a need to develop small molecules as safe and stable immunogens, with minimal adverse side effects, for treating autoimmune diseases, particularly disease associated with abnormal inflammation.

SUMMARY OF THE INVENTION

The present invention provides pharmaceutical compositions including vaccine compositions comprising phosphorylcholine (PC) conjugates and uses thereof for treatment and/or prevention of autoimmune diseases and disorders, such as, rheumatoid arthritis, lupus, multiple sclerosis, and inflammatory bowel disease.

The present invention is based in part on the unexpected discovery that PC-conjugates, such as, PC-OVA, MPC and PC-tuftsin, exhibited an inhibitory effect on the development and progression of systemic lupus erythematosus (SLE) in vivo. Another unexpected finding on which the present invention is founded, is that PC-tuftsin ameliorates, in vivo, the development of inflammatory bowel disease.

According to some embodiments, the present invention provides a phosphorylcholine-conjugate comprising at least one phosphorylcholine moiety or a derivative thereof and at least one carrier selected from the group consisting of a monosaccharide, an oligosaccharide, a glycoprotein, a polysaccharide, a peptide and a lipid.

According to some embodiments, the at least one carrier is selected from tuftsin and a glycan.

According to some embodiments the at least one carrier is a glycan. According to some embodiments, the glycan is an N-type glycan or an O-type glycan. According to some embodiments, the glycan is an N-type glycan comprising at least one of N-acetyl glucosamine and Galβ1-4[Fucα1-3]GlcNAc. According to some embodiments, the phosphorylcholine-glycan conjugate further comprises ES-62.

According to some embodiments the at least one carrier is tuftsin.

According to some embodiments the phosphorylcholine-conjugate comprises one phosphorylcholine moiety or a derivative thereof linked to the carrier.

According to some embodiments the phosphorylcholine-conjugate comprises a plurality of phosphorylcholine moieties or derivatives thereof linked to the carrier.

According to some embodiments the phosphorylcholine-conjugate comprises a plurality of carriers linked to a phosphorylcholine moiety or a derivative thereof.

According to some embodiments the phosphorylcholine moiety or derivative thereof and the carrier are separated by a spacer.

According to some embodiments the present invention provides a pharmaceutical composition comprising a phosphorylcholine-conjugate comprising at least one phosphorylcholine moiety or a derivative thereof linked to at least one carrier selected from tuftsin and a glycan, and further comprising a pharmaceutically acceptable diluents or carriers.

According to some embodiments said pharmaceutical composition is a vaccine. According to some embodiments said pharmaceutical composition further comprises an adjuvant. According to some embodiments the adjuvant is selected from the group consisting of water in oil emulsions, oil in water emulsions and liposomes.

According to some embodiments the present invention provides a method for treating an autoimmune disease in a subject in need thereof comprising administering to the subject a vaccine composition comprising a phosphorylcholine-conjugate comprising at least one phosphorylcholine moiety or a derivative thereof and at least one carrier selected from the group consisting of a polymer, a monosaccharide, an oligosaccharide, a polysaccharide, a peptide, a polypeptide and a lipid, thereby modulating said subject immune response towards an anti-inflammatory phenotype.

According to some embodiments said treating comprises at least one of preventing the onset of said autoimmune disease, attenuating the progress of said autoimmune disease and inhibiting the progression of said autoimmune disease.

According to some embodiments said subject is having a high risk of developing said autoimmune disease. According to some embodiments the autoimmune disease is associated with abnormal inflammation. According to some embodiments the autoimmune disease is selected from the group consisting of rheumatoid arthritis, lupus, multiple sclerosis, pemphigus vulgaris, antiphospholipid syndrome, psoriasis, autoimmune hepatitis, sarcoidosis, inflammatory bowel disease, colitis, Crohn's disease and chronic obstructive pulmonary disease.

According to some embodiments the vaccine composition is administered in a route of administration selected from the group consisting of intravenous, intramuscular, oral, sublingual, intramucosal, intraperitoneal, nasal, subcutaneous, topical, intradermal or transdermal.

According to some embodiments the subject is a mammal. According to some embodiments the subject is human.

According to some embodiments the autoimmune disease is lupus. According to some embodiments the carrier is selected from the group consisting of ovalbumin, tuftsin and 2-methacryloyloxyethyl. According to some embodiments the phosphorylcholine-conjugate comprises at least one of phosphorylcholine-tuftsin, phosphorylcholine-ovalbumin and 2-methacryloyloxyethyl-phosphorylcholine.

According to some embodiments the autoimmune disease is colitis. According to some embodiments the carrier is tuftsin. According to some embodiments the phosphorylcholine-conjugate is phosphorylcholine-tuftsin.

According to some embodiments the autoimmune disease is rheumatoid arthritis. According to some embodiments the carrier is selected from the group consisting of tuftsin, glycan and 2-methacryloyloxyethyl. According to some embodiments the PC-conjugate comprises at least one of phosphorylcholine-tuftsin, phosphorylcholine-glycan and 2-methacryloyloxyethyl-phosphorylcholine.

According to some embodiments the present invention provides a use of a vaccine composition comprising a phosphorylcholine-conjugate comprising at least one phosphorylcholine moiety or a derivative thereof and at least one carrier selected from the group consisting of a polymer, a monosaccharide, an oligosaccharide, a polysaccharide, a peptide, a polypeptide and a lipid, for the treatment of an autoimmune disease.

According to some embodiments the present invention provides a kit for the treatment of an autoimmune disease comprising a vaccine composition comprising a phosphorylcholine-conjugate comprising at least one phosphorylcholine moiety or a derivative thereof and at least one carrier selected from the group consisting of a polymer, a monosaccharide, an oligosaccharide, a polysaccharide, a peptide, a polypeptide and a lipid.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 3A-3B show kidney sections of lupus mice treated with PC-OVA probed with anti-mouse IgG-FITC Fc specific antibodies (FIG. 3A) stained with Periodic acid-Schiff (PAS; FIG. 3B)

FIGS. 4A-4B show kidney sections of lupus mice treated with MPC probed with anti-mouse IgG-FITC Fc specific antibodies (FIG. 4A) stained with Periodic acid-Schiff (PAS; FIG. 4B).

FIGS. 5A-5C show kidney sections of control lupus mice treated with PBS probed with anti-mouse IgG-FITC Fc specific antibodies (FIG. 5A) stained with Periodic acid-Schiff (PAS; FIG. 5B and FIG. 5C).

FIG. 8A) or PC-tuftsin (FIG. 8B).

FIG. 9A) or PC-tuftsin (FIG. 9B) probed with anti-mouse IgG-FITC Fc specific antibodies.

FIG. 13A; p<0.02), rectal bleeding (FIG. 13B; p<0.001), weight loss (relative to t=0; FIG. 13C; p<0.001) and survival (FIG. 13D) in mice subjected to DSS induction of inflammatory bowel disease ("IBD mice") following treatment with PC-tuftsin (empty circle) and PBS (solid circle).

FIG. 15A, FIG. 15E) or PC-tuftsin (FIG. 15B, FIG. 15F) as compared to a colon section from a mouse not subjected to DSS induction of IBD (FIG. 15C, FIG. 15G).

DETAILED DESCRIPTION OF THE INVENTION

Figure 1:
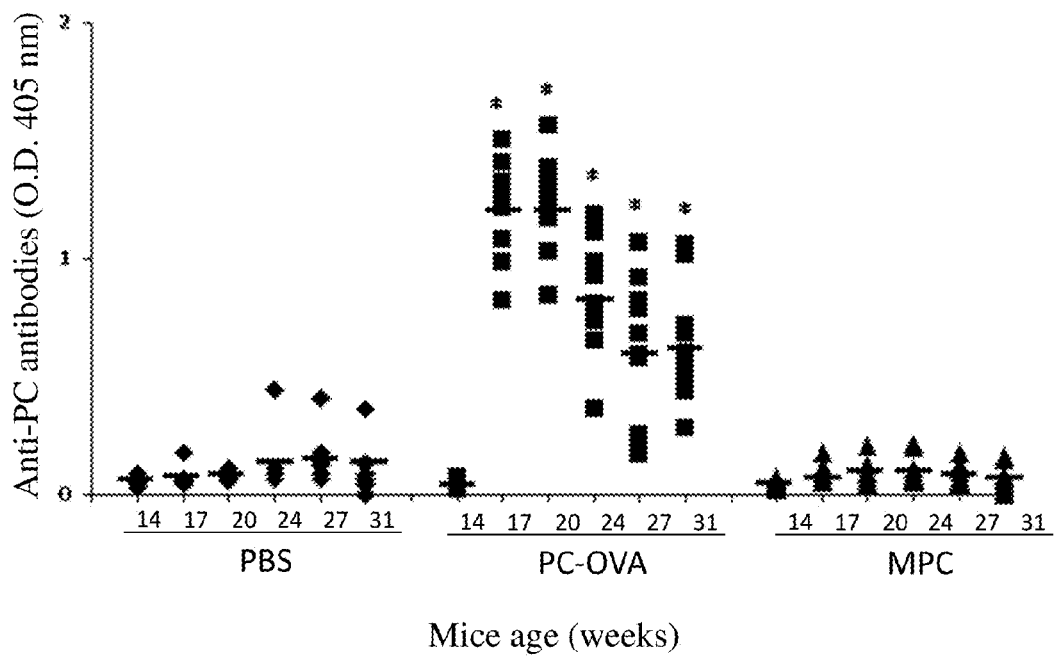
FIG. 1 shows the level of anti-PC antibodies (in units of Optical Density, O.D., at 405 nm) in the sera of NZBxNZW/F1 mice ("lupus mice") treated with PC-OVA (square; *=$p<0.001$), MPC (triangle; $p>0.05$) or PBS (control; diamond).

The present invention provides pharmaceutical compositions, including vaccine compositions, comprising at least one phosphorylcholine (PC)-conjugate. According to some embodiments, the pharmaceutical compositions of the invention exhibit an immunomodulatory activity. According to some embodiments, the pharmaceutical compositions are for treating, ameliorating the progress of, and preventing onset of, autoimmune diseases. According to some embodiments, the PC-conjugates of the present invention are produced synthetically to ensure the stability and reproducibility of these compounds, while maintaining or even enhancing their activity. According to some embodiments, PC-conjugates are useful as stimulators of a subject immune system towards the Th2 phenotype.

As used herein, the terms "immunomodulation", "immunomodulation activity", "immunomodulatory activity" or "modulating the immune response" with reference to the PC-conjugates of the present invention refer to the ability of the conjugates to elicit at least one of: reducing the ability of lymphocytes (both B– and T–) to proliferate in response to antigen; inducing generation of T and/or B regulatory (suppressor) cells; and affecting macrophages and dendritic cell functions. Affecting macrophages and dendritic cell functions includes but is not limited to, stimulating clearance of apoptotic cells and inducing tolerogenic dendritic cells; inhibiting the ability of macrophages to produce pro-inflammatory cytokines such as IL-12, TNF-α and IL-6; modulating dendritic cell maturation to preferentially elicit Th2-like responses; and inducing spleen cells to produce the anti-inflammatory cytokine, IL-10 and to bias antibody responses in a Th2/anti-inflammatory direction. The immunomodulatory activity of the PC-conjugates may be also referred to herein as "anti-inflammatory" activity.

The term "phosphorylcholine (PC) conjugate" as used herein, refers to a phosphorylcholine moiety linked to a carrier, optionally via a spacer. The structural element phosphorylcholine may comprise a derivative of phosphorylcholine. The carrier may be a peptide, a polypeptide, a monosaccharide, an oligosaccharide, a polysaccharide, a glycoprotein, a lipid, a polymer and the like. Each possibility is a separate embodiment of the invention.

As used herein, the term "derivative of phosphorylcholine" including but not limited to, the following: 4-aminophenylphosphocholine, 4-diazoniophenylphosphorylcholine, 4-nitrophenylphosphocholine and 12-(3-Iodophenyl) dodecylphosphocholine among others. Each possibility is a separate embodiment of the invention.

The carrier may be immunogenic or non-immunogenic.

As used herein, the term "immunogenic carrier" refers to a variety of molecules or substances that are capable of inducing an immune response against the PC molecule.

According to other embodiments, the carrier is a glycoprotein or an immunogenic polymer molecule. PC is expressed by a diverse range of organisms. In the Gram-positive bacterium *Streptococcus pneumonia* PC is attached directly to sugar residues, generally considered to be N-acetylgalactosamine. PC has been detected also in a wide range of Gram-positive bacteria including *Clostridium, Lactococcus, Bacillus* and the Gram-negative bacterium *Haemophilus influenzae*. Eukaryotic organisms in which PC has been detected include many important disease-causing agents such as the protozoa *Leishmania major* and *Trypanosoma cruzi*; a wide range of fungi; the trematode *Schistosoma mansoni*; the tapeworm *Diphyllobothrium latum*; several gastrointestinal nematodes and all species of filarial nematode. In human, PC appear on the inner leaflet of a cell membrane and is exposed to the immune system by apoptotic cells.

The term "non-immunogenic carrier" as used herein refers to a variety of molecules or substances that do not elicit an immune response.

According to some embodiments the PC-conjugate is selected from the group consisting of PC-tuftsin and PC-glycan.

According to other embodiments the PC-conjugate is PC-tuftsin.

As used herein, the term "tuftsin" refers to a tetrapeptide (threonine-lysine-proline-arginine, TKPR; SEQ ID NO: 17). Tuftsin may be synthesized chemically or isolated from the spleen by enzymatic cleavage of the Fc domain of IgG heavy chain. Tuftsin is known for its phagocytosis-stimulating activity and augmentation of antigen presenting capacity of macrophages in-vitro and in-vivo. According to some embodiments, tuftsin may be considered as an adjuvant. It is to be understood that tuftsin refers to tuftsin and derivatives thereof, including but not limited to, the following: threonine-lysine-proline TKP; TKPXaa; (SEQ ID NO: 18), threonine-lysine-proline-proline-arginine (TKPPR; SEQ ID NO: 19), serine-lysine-proline-arginine (SKPR; SEQ ID NO: 20), threonine-arginine-proline-arginine (TRPR; SEQ ID NO: 21) and serine-lysine-proline-lysine (SKPK; SEQ ID NO: 22) among others. Each possibility is a separate embodiment of the invention.

According to some embodiments, the PC-conjugate is PC-glycan.

According to some embodiments, the term "glycan" refers to N-type glycan and O-type glycan. Each possibility is a separate embodiment of the invention.

As used herein, the terms "N-type glycan" and "N-glycan" are interchangeable and refer to a glycan which is covalently bonded to a substrate, such as PC, by an N-glycosidic linkage. Any type of N-glycan may be used to form the PC-conjugate of the present invention.

According to some embodiments, the PC is conjugated to the N-type glycan is N-acetyl glucosamine (GlcNAc) and Galβ1-4[Fucα1-3]GlcNAc among others. Each possibility is a separate embodiment of the invention.

As used herein, the terms "O-type glycan" and "O-glycan" are interchangeable and refer to a glycan which is covalently bonded to a substrate, such as PC, by an O-glycosidic linkage. Any type of O-glycan may be used to form the PC-conjugate of the present invention.

According to some embodiments, the PC conjugated to the O-type glycan is —N-Acetyl galactosamine (GalNAc) and α-D-Gal-(1→3)-(α-L-Fuc-[1→2])-D-Gal among others. Each possibility is a separate embodiment of the invention.

According to some embodiments the glycan comprises monosaccharides selected from the group consisting of N-acetyl glucosamine, N-Acetyl galactosamine, galactose, sialic acid, glucose, fucose and mannose among others. Each possibility is a separate embodiment of the invention.

According to other embodiments, the PC-conjugate is PC-glycan which further comprises ES-62.

The term "ES-62" refers to a tetrameric glycoprotein (62 kDa subunits) attached to phosphorylcholine (PC) moieties via an N-type glycan. ES-62 is secreted by the rodent filarial nematode *Acanthocheilonema viteae* and found to have orthologs in human filarial nematode parasites including *Brugia malayi* and *Onchocerca volvulus*. ES-62 acts to bias the immune response toward an anti-inflammatory/Th2 phenotype that is beneficial to both worm survival and host health. For example, although ES-62 initially induces macrophages to produce low levels of IL-12 and TNFα, exposure to the parasite product ultimately renders the cells unable to produce these cytokines in response to classic stimulators such as LPS/IFNγ. The molecule is able to directly interact with a number of cells of the immune system including B-lymphocytes, dendritic cells, macrophages and mast cells. Interaction appears to be dependent on producing a complex with Toll-like receptor 4 (TLR4) and results in modulation of the activity of a number of signal transduction molecules including MAP kinases, PI-3 kinase and NF-κB.

Examples of the effect of parasitic helminthes in autoimmune disease include a study in patients with active ulcerative colitis and Crohn's disease treated by ingestion of live eggs of pig helminths *Trichuris suis*. In this study, the disease remitted after consumption of the eggs. Furthermore, employing experimental autoimmune models, amelioration of disease activity was achieved by helminths or helminths derivatives administration. In addition, studies with non-obese diabetic (NOD) mice showed that inoculation with *Trichinella spiralis, Heligmosomoides polygyrus*, or *Schistosoma mansoni*, using egg antigen or the worm antigen markedly reduced the rate of experimental type-I diabetes mellitus (T1DM) and suppressed lymphoid infiltration in the islets of the pancreas. Moreover, amelioration of experimental autoimmune encephalomyelitis (EAE) was achieved upon helminthes treatment; *Schistosome* worm infections prevented colitis, shifting the immune response towards the Th2 phenotype; and *Syphacia oblevata* infected rats developed less severe arthritis than uninfected rats. Extract of the nematodes *Ascaris suum, Schistosoma mansoni* and *Acanthocheilonema viteae* were also found to reduce the severity of collagen induced arthritis (CIA) in mice.

According to some embodiments, the present invention provides a phosphorylcholine (PC)-conjugate comprising at least one phosphorylcholine moiety or a derivative thereof linked to at least one carrier selected from the group consisting of a peptide, a polypeptide, a lipid, a polysaccharide, a monosaccharide, an oligosaccharide and a polymer. Each possibility is a separate embodiment of the invention.

According to some embodiments, the phosphorylcholine-conjugate comprises one PC moiety or a derivative thereof linked to a carrier.

According to other embodiments, the phosphorylcholine-conjugate comprises a plurality of PC moieties or derivatives thereof linked to the carrier.

According to other embodiments, the phosphorylcholine-conjugate comprises a plurality of carriers linked to a single PC moiety or a derivative thereof.

According to some embodiments, the phosphorylcholine-conjugate is consisting of at least one PC moiety or a derivative thereof and at least one carrier selected from the group consisting of a monosaccharide, an oligosaccharide, a polysaccharide, a peptide and a lipid. Each possibility is a separate embodiment of the invention.

According to additional embodiments, the phosphorylcholine moiety or derivative thereof and the carrier are separated by a spacer.

The term "spacer", as used herein, refers to a connecting or otherwise bridging element between a carrier and the PC moiety, typically linked by chemical methods or biological means thereto. Non-limiting examples of spacer include: amino acids, peptides, polypeptides, proteins, hydrocarbons and polymers among others. Each possibility is a separate embodiment of the invention.

According to some embodiments, the PC-conjugate comprises PC and a carrier, linked to one another.

As used herein, the term "linked" refers to attached, connected, bound to, in association with and coupled to, among others.

According to some embodiments, the PC and the carrier are linked through a covalent bond.

According to additional embodiments, the synthetic PC-conjugates of the present invention may be synthesized as described in the Example section hereinbelow.

According to some embodiments, the present invention provides a pharmaceutical composition comprising a phosphorylcholine-conjugate comprising at least one PC moiety or a derivative thereof linked to at least one carrier selected from tuftsin and a glycan, and further comprising a pharmaceutically acceptable carriers, excipients, or diluents.

According to other embodiments, the pharmaceutical composition is in the form of solution, suspension, tablets, chewable tablets, capsules, syrups, intranasal sprays, suppositories, transdermal patches, among other types of pharmaceutical compositions. Each possibility is a separate embodiment of the invention.

According to other embodiments, the pharmaceutical composition is a long acting, controlled release, extended release or slow release formulation. Each possibility is a separate embodiment of the invention.

According to additional embodiments, the pharmaceutical composition is a vaccine. The term "vaccine" as used herein, refers to a product, the administration of which is intended to elicit an immune response that is capable of preventing and/or lessening the severity of one or more autoimmune diseases or disorders and inflammation among other diseases and disorders. Each possibility is a separate embodiment of the invention.

According to additional embodiments, the present invention provides a vaccine composition comprising at least one PC-conjugate. The vaccine is effective in preventing, treating or reducing the progression of an autoimmune disease. Each possibility is a separate embodiment of the invention.

The PC-conjugates of the invention may be administered prophylactically as vaccines. The vaccines of the invention contain as an active ingredient at least one conjugate of phosphorylcholine and a carrier. Useful pharmaceutically acceptable carriers are well known in the art, and include, for example, thyroglobulin, albumins such as human serum albumin, tetanus toxoid, polyamino acids such as poly(D-lysine:D-glutamic acid), influenza, hepatitis B virus core protein and hepatitis B virus recombinant vaccine. Each possibility is a separate embodiment of the invention.

The vaccines may also contain a physiologically tolerable (acceptable) diluent such as water, phosphate buffered saline, or saline, and may further include an adjuvant. Each possibility is a separate embodiment of the invention.

According to some embodiments the vaccine further comprising an adjuvant. The term "adjuvant" as used here refers to a pharmacological and/or immunological agent that modifies the effect of other agents and specifically, enhances the immune response to an antigen. Adjuvants may be inorganic or organic chemicals, macromolecules or entire cells of certain bacteria. Each possibility is a separate embodiment of the invention.

According to some embodiments the adjuvant is selected from the group consisting of water in oil emulsions, oil in water emulsions, liposomes, incomplete Freund's adjuvant, aluminum phosphate, aluminum hydroxide and alum, among others. Each possibility is a separate embodiment of the invention.

The pharmaceutical compositions of the invention are suitable for use in a variety of drug delivery systems as detailed hereinbelow. Pharmaceutically acceptable carriers suitable for use in the present invention may be found in Remington's Pharmaceutical Sciences, Mack Publishing Company, Philadelphia, Pa., 17th ed. (1985).

According to additional embodiments, the present invention provides a method for treating an autoimmune disease in a subject in need thereof comprising administering to the subject a vaccine composition comprising at least one PC-conjugate wherein the PC-conjugate comprises at least one PC moiety or a derivative thereof and at least one carrier selected from the group consisting of a monosaccharide, an oligosaccharide, a glycoprotein, a polysaccharide, a peptide and a lipid, thereby, modulating the immune response of said subject towards an anti-inflammatory phenotype. Each possibility is a separate embodiment of the invention.

According to some embodiments, the present invention provides use of a vaccine composition comprising a phosphorylcholine-conjugate comprising at least one PC moiety or a derivative thereof and at least one carrier selected from the group consisting of a polymer, a monosaccharide, an oligosaccharide, a polysaccharide, a peptide, a polypeptide and a lipid for the treatment of an autoimmune disease. Each possibility is a separate embodiment of the invention.

As used herein, the terms "treating" or "treatment" are interchangeable and refer to any one or more of preventing the onset of an autoimmune disease, attenuating the progress of said autoimmune disease and inhibiting the progression of an autoimmune disease, among others.

According to some embodiments, the subject in need thereof is a mammal. According to some embodiments, the subject in need thereof is human.

According to some embodiments, the method of the invention comprises the steps of (i) determining the risk of a subject for an autoimmune disease; (ii) selecting a subject having a risk for said disease; and (iii) treating said subject having the risk with the PC-conjugate of the invention.

According to further embodiments, the autoimmune disease is associated with abnormal inflammation. According to further embodiments, the disease or disorder is an autoimmune disease. According to further embodiments, the autoimmune disease is selected from the group consisting of rheumatoid arthritis, lupus, multiple sclerosis, autoimmune skin disorders including pemphigus vulgaris and psoriasis, antiphospholipid syndrome, autoimmune hepatitis, sarcoidosis, colitis, inflammatory bowel disease, including, Crohn's disease and chronic obstructive pulmonary disease. Each possibility represents a separate embodiment of the present invention.

Lupus, or lupus erythematosus, as used herein, refer to a category for a collection of systemic autoimmune diseases. Symptoms of these diseases may affect many different body systems, including joints, skin, kidneys, blood cells, heart, and lungs. Four main types of lupus are known to date: systemic lupus erythematosus, discoid lupus erythematosus, drug-induced lupus erythematosus, and neonatal lupus erythematosus. Of these, systemic lupus erythematosus is the most common and serious form of lupus. The abnormal immune response allows sustained production of pathogenic autoantibodies and immune complexes that cause damage to the various tissues and systems. The abnormal immune response probably depends upon the interaction of multiple hereditary and environmental factors.

According to some embodiments, the method of the invention is for treating lupus wherein the carrier of the PC-conjugate is one or more of ovalbumin, tuftsin, and 2-methacryloyloxyethyl. Each possibility is a separate embodiment of the invention.

According to some embodiments, the method of the invention is for treating lupus wherein the PC-conjugate is one or more of PC-tuftsin, PC-ovalbumin and 2-methacryloyloxyethyl-PC. Each possibility is a separate embodiment of the invention.

The terms "rheumatoid arthritis" and "RA", as used herein are interchangeable and refer to a chronic disease featuring persistent inflammatory synovitis, typically involving peripheral joints in a symmetric distribution. This inflammation may lead to bone erosions, cartilage damage and joint destruction. It is an affliction of about 1% of the population. The prevalence increases with age, and women are affected more frequently than men. The propagation of RA is an immunologically mediated event driven by CD4$^+$ Th1 cells.

According to some embodiments, the method of the invention is for treating rheumatoid arthritis wherein the carrier of the PC-conjugate is one or more of tuftsin, glycan and 2-methacryloyloxyethyl. Each possibility is a separate embodiment of the invention.

According to some embodiments, the method of the invention is for treating rheumatoid arthritis wherein the PC-conjugate is one or more of PC-tuftsin, PC-glycan and 2-methacryloyloxyethyl-PC. Each possibility is a separate embodiment of the invention.

The terms "Multiple sclerosis" and "MS", as used herein are interchangeable and typically refer to a chronic relapsing, multifocal inflammatory disorder of the central nervous system that leads to focal demyelination and scarring of the brain. It is a frequent disease affecting about 350,000 Americans, manifesting during early to middle adulthood. MS is an autoimmune disease mediated at least in part by Th1 cells. The lesions of MS resemble those induced by delayed hypersensitivity responses that contain activated T cells and macrophages. Experimental autoimmune encephalomyelitis, also named Experimental Allergic Encephalomyelitis (EAE) is an animal model of brain inflammation. It is an inflammatory demyelinating disease of the central nervous system (CNS). It is mostly used with rodents and is widely studied as an animal model of the human CNS demyelinating diseases, including the diseases multiple sclerosis and acute disseminated encephalomyelitis (ADEM). EAE is also the prototype for T-cell-mediated autoimmune disease in general.

The term "colitis" as used herein refers to any one or more of the following diseases and disorders: inflammatory bowel disease (IBD), Crohn's disease, ulcerative colitis, collagenous colitis, lymphocytic colitis, ischemic colitis, diversion colitis, Behcet's disease and indeterminate colitis, among others.

While the cause of IBD remains undetermined, it is presumed to result from dysregulation of the intestinal mucosal immune system. Inflammatory cells in the mucosa normally have a protective effect against luminal contents. This highly effective chronic inflammation is tightly controlled to limit tissue injury. IBD may result from inappropriately vigorous immune responses to luminal factors. Crohn's disease (CD) appears to be an overly vigorous Th-type inflammation that produces IFNγ and TNFα. The incidence of Crohn's disease in industrialized societies has increased from the 1950s until the mid-1980s, and now is about 1 to 8 cases per 100,000 persons per year. This suggests that unknown changes in our environment have affected the frequency of Crohn's disease. The nature of ulcerative colitis (UC) is less well defined.

There are several animal models of chronic intestinal inflammation. In fact, mice with genetically engineered gene deletions may develop chronic bowel inflammation similar to IBD. These include mutant mice bearing targeted deletions for IL-2, IL-10, and MHC class II or TCR genes among others. It was shown in some animal models that a dysregulated immune system itself can mediate intestinal injury. The mucosal inflammation in several animal models generates large amounts of IFNγ and TNFα, suggesting that excess production of Th1-type cytokines is one common mechanism underlying the pathogenesis of disease. Also, blocking Th1 circuitry prevents the inflammation. CD is a Th1 response. Thus, these models may have direct implications in the immunopathology of this human disease process.

According to some embodiments, the method of the invention is for treating colitis wherein the carrier of the PC-conjugate is tuftsin.

According to some embodiments, the method of the invention is for treating colitis wherein the PC-conjugate is PC-tuftsin.

According to some embodiments, the disease or disorder is an autoimmune skin disorder. There are many different types of skin-related autoimmune disorders, including, for example scleroderma, psoriasis, dermatomyositis, epidermolysis bullosa and bullous pemphigoid. Pemphigus vulgaris is a chronic blistering skin disease with skin lesions that are rarely pruritic, but which are often painful. The disease is caused by antibodies directed against both desmoglein 1 and desmoglein 3 resulting in the loss of cohesion between keratinocytes in the epidermis. It is characterized by extensive flaccid blisters and mucocutaneous erosions. Psoriasis occurs when the immune system mistakes the skin cells as a pathogen, and sends out faulty signals that speed up the growth cycle of skin cells. The disorder is a chronic recurring condition that varies in severity from minor localized patches to complete body coverage. Fingernails and toenails are frequently affected (psoriatic nail dystrophy) and may be seen as an isolated symptom. Psoriasis may also cause inflammation of the joints, which is known as psoriatic arthritis.

According to further embodiments, the vaccine composition is administered in a route of administration selected from the group consisting of intravenous, intramuscular, oral, sublingual, intramucosal, intraperitoneal, nasal, subcutaneous, topical and intradermal or transdermal. Each possibility represents a separate embodiment of the present invention.

Thus, the invention provides compositions for parenteral administration that comprise a solution of the agents described above dissolved or suspended in an acceptable carrier, such as an aqueous carrier. A variety of pharmaceutically acceptable aqueous carriers may be used, e.g., water, buffered water, 0.4% saline, 0.3% glycine hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. Each possibility is a separate embodiment of the invention.

The pharmaceutical compositions of the invention may be in the solid state. For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. Pharmaceutical formulations suitable for oral administration wherein the excipient is solid are, for example, presented as unit dose formulations such as boluses, capsules or tablets each containing a predetermined amount of the PC-conjugate of the invention as the active compound. A tablet may be made by compression or molding, optionally with one or more accessory ingredients. Compressed tablets may be prepared by compressing in a suitable machine the active compound in a free-flowing form such as a powder or granules optionally mixed with a binder, lubricant, inert diluents, lubricating agent, surface-active agent or dispersing agent. Molded tablets may be made by molding the active compound with inert liquid diluents. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may, for example, be suspended in water before administration, or sprinkled on food. The granules may be packaged, e.g., in a sachet.

For aerosol administration, the pharmaceutical compositions of the invention are, for example, supplied in finely divided form along with a surfactant and optionally a propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Each possibility is a separate embodiment of the invention. Mixed esters, such as mixed or natural glycerides, may be employed. A carrier may also be included, as desired, as with, e.g., lecithin for intranasal delivery.

The pharmaceutical compositions of the invention may be in the form liposome. Liposomes provide another delivery system for the delivery and presentation of the immunomodulatory molecules of the invention. Liposomes are bilayer vesicles composed of phospholipids and other sterols surrounding a typically aqueous center where the PC-conjugate or other products may be encapsulated. The liposome structure is highly versatile with many types range in nanometer to micrometer sizes, from about 25 nm to about 500 µm. Liposomes have been found to be effective in delivering therapeutic agents to dermal and mucosal surfaces. Liposomes may be further modified for targeted delivery by, for example, incorporating specific antibodies into the surface membrane. The average survival time or half-life of the intact liposome structure may be extended with the inclusion of certain polymers, such as polyethylene glycol, allowing for prolonged release in vivo. Liposomes may be unilamellar or multilamellar.

The pharmaceutical compositions of the invention may be in the form of microparticles and nanoparticles. Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug delivery. The rates of copolymer hydrolysis are very well characterized, which in turn allows for the manufacture of microparticles with sustained release of the immunomodulators over prolonged periods of time.

The pharmaceutical compositions of the invention may be parenteral administered as microparticles. Microparticles elicits long-lasting immunity, especially if they incorporate prolonged release characteristics. The rate of release may be modulated by the mixture of polymers and their relative molecular weights, which will hydrolyze over varying periods of time. Without wishing to be bound to theory, the formulation of different sized particles (1 µm to 200 µm) may also contribute to long-lasting immunological responses since large particles must be broken down into smaller particles before being available for macrophage uptake. In this manner a single-injection vaccine could be developed by integrating various particle sizes, thereby prolonging PC-conjugate presentation.

Vaccine compositions containing the PC-conjugates of the invention are administered to a patient to elicit modulation of the subject's immune response towards anti-inflammatory activity as defined herein. An amount sufficient to accomplish the desired therapeutic activity is defined as an "immunomodulatory effective dose." Amounts effective for this use will depend on, e.g., the PC-conjugate composition, the manner of administration, the weight and general state of health of the patient, as well as the judgment of the prescribing physician.

The PC-conjugates of the present invention can be used in pharmaceutical vaccine comprising the PC-conjugates and pharmaceutically acceptable carriers. These compositions are suitable for single administrations or a series of administrations (immunization schedules). When given as a series, inoculations subsequent to the initial administration are given to boost the immune response and are typically referred to as booster inoculations.

When an immunization schedule calls for two or more separate dosing, it is necessary to consider the intervals between doses. The interval between two successive doses may be the same or it may change throughout the program. According to certain embodiments, the immunization schedule further comprises re-exposure of the subject to the vaccine comprising the PC-conjugate of the present invention (booster dose). As is known to those skilled in the art, a variety of possible combinations and subcombinations of the various preferred conditions of timing of the first administration, shortest interval, largest interval and total number of administrations (in absolute terms, or within a stated period) exist. It is to be understood that all of these combinations and subcombinations are within the teachings of the present invention.

The invention also provides a kit for the treatment of an autoimmune disease comprising one or more containers filled with the vaccine composition comprising a phosphorylcholine-conjugate comprising at least one PC moiety or a derivative thereof and at least one carrier selected from the group consisting of a polymer, a monosaccharide, an oligosaccharide, a polysaccharide, a peptide, a polypeptide and a lipid. Optionally associated with such container(s) may be a notice in the form described by a governmental agency regulating the manufacture, use or sale of pharmaceuticals or biological products, which notice reflects approval by the agency of manufacture, use or sale for human administration.

According to some embodiments, the present invention provides a kit for the treatment of an autoimmune disease or disorder, the kit comprising a first container comprising a phosphorylcholine-conjugate comprising at least one PC moiety or a derivative thereof and at least one carrier selected from the group consisting of a polymer, a monosaccharide, an oligosaccharide, a polysaccharide, a peptide, a polypeptide and a lipid; a second container comprising a pharmaceutically acceptable carriers, diluents or excipients; and, optionally, a third container comprising an adjuvant. The kit may further comprise a protocol for preparing a vaccine from the contents of said first and second container, and optionally, also from the contents of said third container.

The PC-conjugates of the invention are useful in vaccines and in immunization protocols for prevention, treatment and progress inhibition of autoimmune diseases, particularly inflammatory diseases.

According to some embodiments, the PC-conjugates of the present invention, when administered to a mammal, elicit the mammal's immunomodulation activity. A variety of models known to those skilled in the art may be used to establish the immunomodulation ability of the conjugates of the invention. Cell cultures may be used to test the effect of the PC-conjugates on cell proliferation, cytokine profile, development of tolerogenic dendritic cells and development of T regulatory cell. For example, commercial kits for following pro- and anti-inflammatory cytokine, including, but not limited to IL-1, IL-2, IFNγ, IL-4, IL-10, IL-15, IL-17 and TNFα may be used. Animal models, as are known to a person skilled in the art and as exemplified herein below, may be used to test the activity of the PC-conjugates of the invention in treating, preventing or reducing the progression of autoimmune diseases.

According to some embodiments, the immunomodulation capability of the PC-conjugates of the present invention are exemplified hereinbelow in animal models of autoimmune diseases, including collagen induced arthritis (CIA), colitis and systemic lupus erythematosus (SLE).

The examples hereinbelow are presented in order to more fully illustrate some embodiments of the invention. They should, in no way be construed, however, as limiting the broad scope of the invention. One skilled in the art may readily devise many variations and modifications of the principles disclosed herein without departing from the scope of the invention.

EXAMPLES

Example 1: The Effect of PC-Conjugates on the Development of Systemic Lupus Erythematosus (SLE)

Phospholipids are non-immunogenic. Therefore, phosphorylcholine (PC) is commonly used as a conjugate to different carriers. The carriers may serve as adjuvant. The following PC-conjugates were used in the current study: PC-Ovalbumin (PC-OVA) and 2-methacryloyloxyethyl-PC (MPC).

PC-OVA was purchased from Biosearch Technologies, Inc.

In MPC, the PC appears as a moiety on the helminthes. Specifically, MPC is PC-moiety on polymer (2-methacryloyloxyethyl) core defined as MPC. MPC was purchased from NOF Inc.

The potential of PC-conjugates to immunomodulate lupus was studied in NZBxNZW/F1 mice which develop lupus on a genetic background.

Mice: female NZBxNZW/F1 mice were obtained from Harlan Olac, and supplied by Jackson Laboratory (Bar Harbor, USA) at the age of 8-10 weeks. The mice were maintained at the Sheba animal facilities, Sheba Medical Center, Israel. All animals were cared for as approved by the Ethical Review Committee of the Israeli Ministry of Health and Sciences animal guidelines.

The serological and clinical manifestation of lupus nephritis in NZBxNZW/F1 mice was assessed as previously described (Shoenfeld Y et al., Int Immunol. 2002, 14(11): 1303-1311). Briefly, antibodies specific for PC were measured by ELISA as described hereinbelow. Antibodies specific for dsDNA were detected by ELISA as previously described by us (Shoenfeld et al., 2002, ibid). Proteinuria was measured by a standard semi-quantitative test using an Albustix kit (Bayer Diagnostic). Renal immune complex deposits (ICD) were determined as previously described (Shoenfeld et al., 2002, ibid). The intensity of the ICD was graded as follows: 0, no ICD; 1, low intensity; 2, moderate intensity; and 3, high intensity of ICD. ICD analysis was performed by two subjects unaware whether or not each mouse is a treatment mouse or a control mouse.

The results demonstrate the inhibitory effect of PC-OVA and MPC treatments on the development of lupus nephritis in the NZBxNZW/F1 lupus mice. The inhibitory effect was manifested by postponed proteinuria and decreased immune complex deposits on the glomerular basement membrane. The results are based on treatment at an early stage of the disease starting at week 8 of age. PC-OVA, MPC or PBS were given 3 times a week 3 µg/0.1 ml per mouse subcutaneously, n=20 per group. The mice were bled every 2 weeks for measurement of PC and dsDNA specific antibodies. Proteinuria was assessed every 2 weeks.

Treatment with PC-OVA conjugate (FIG. 1, squares) was immunogenic and the mice developed elevated titers of anti-PC antibodies (p<0.001) in comparison to PBS (FIG. 1, diamonds) and MPC (FIG. 1, triangles) treated group, whereas MPC (poly PC on polymeric core) was non immunogenic and did not cause generation of anti-PC antibodies (p>0.05). Data of the anti-PC antibodies are presented at sera dilution of 1:400. The results are given as O.D. at 405 nm. The presence of PC specific antibodies in the mice sera was detected by ELISA to PC-KLH (PC-Keyhole limpet hemocyanin), where binding to KLH served as a control reference. No response to KLH was observed. PC-OVA and MPC did not have any effect on anti-dsDNA antibodies generation in all time points (data not shown).

No effect of PC-OVA and MPC treatment was documented in anti-dsDNA antibodies generation as illustrated in FIG. 1.

Figure 2:
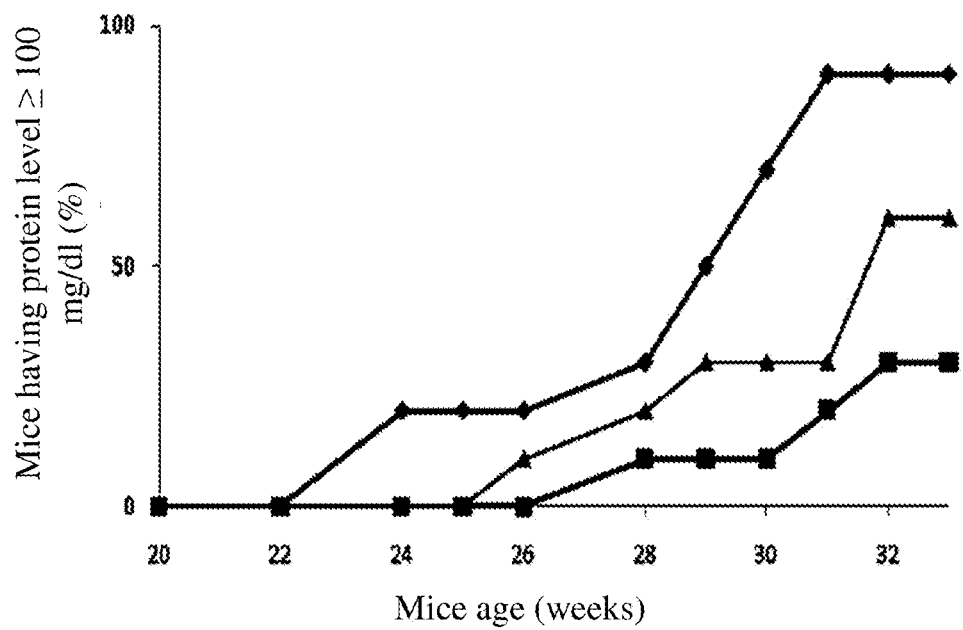
FIG. 2 shows the progression of proteinuria in lupus mice treated with PC-OVA (square), MPC (triangle) or PBS (control; diamond) as the percentage of protein levels of at least 100 mg/dl ($p<0.02$) in the urine.

Proteinuria (defined as at least 100 mg/dl protein in the urine) in lupus mice treated with PC-OVA (FIG. 2, square) or MPC (FIG. 2, triangle) was postponed significantly (p<0.02) in comparison to treatment with PBS (FIG. 2, diamond) at 30 to 33 weeks of age.

Kidney sections from lupus mice treated with PC-OVA (FIGS. 3A-3B), MPC (FIGS. 4A-4B) and PBS (FIGS. 5A-5C) were analyzed for glomerulonephritis. Two staining procedures were applied (i) histological staining (PAS); and (ii) immunohistological staining of immune complex deposits in the mesangium of the kidney using anti-mouse-Fc-FITC conjugate. As illustrated in FIGS. 5A-5C, mice treated with PBS showed severe (stage VI) glomerulonephritis exemplified by strong immune complex deposits (5A), diffused proliferating glomerulonephritis (5B) and crescent necrotizing glomerulonephritis (5C). However, at the same time point of 34 weeks lupus mice treated with MPC (FIGS. 4A-4B) and PC-OVA (FIGS. 3A-3B), exhibited only early stage (stage II) of glomerulonephritis.

Figure 6:
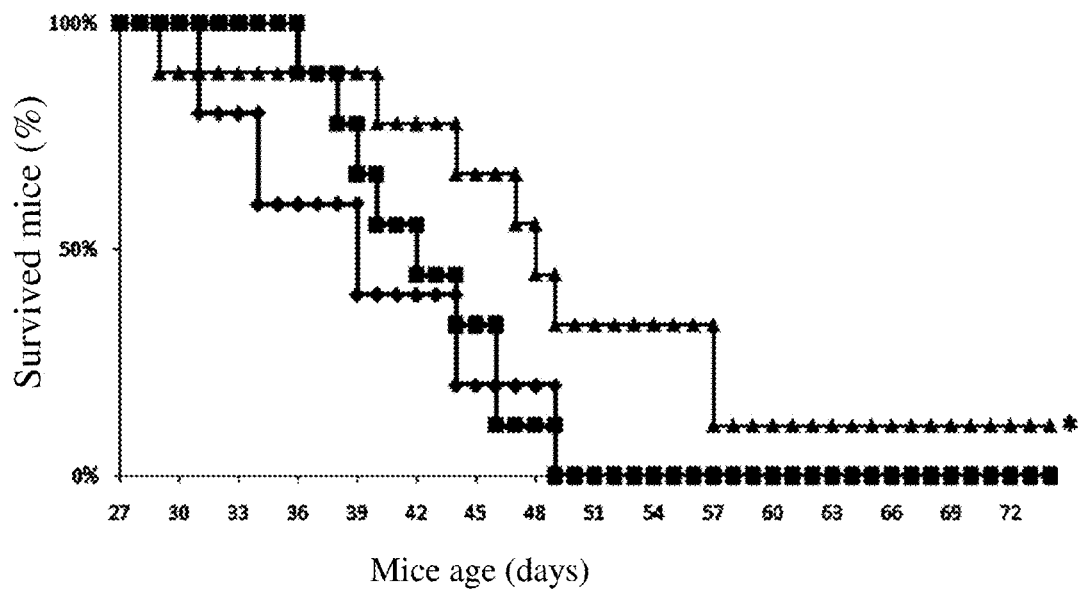
FIG. 6 is a Kaplan-Meier graph demonstrating survival of lupus mice treated with PC-OVA (triangle; *=$p<0.01$), MPC (square; $p<0.04$) or PBS (control; diamond).

A Kaplan-Meier analysis indicates that the survival time of lupus mice treated with PC-OVA (FIG. 6, triangle) was significantly longer (FIG. 6 *=p<0.01) compared to PBS treated mice (FIG. 6, diamond). The survival time of MPC treated mice (FIG. 6, square) showed only tendency of significance (p<0.04).

Example 2: The Effect of PC-Tuftsin on Development of Proteinuria In Vivo

Phospholipids are non-immunogenic, thus, PC was conjugated to PC-tuftsin which may serve as adjuvant.

PC-Tuftsin: Tuftsin is a tetrapeptide (threonine-lysine-proline-arginine, TKPR; SEQ ID NO: 17). In autoimmune models such as EAE and lupus it had an inhibitory effect on disease progression (Dagan S et al., J Biol Response Mod. 1987, 6(6):625-636). PC conjugated to tuftsin is synthesized based on Michaelson Chemistry. The PC derivative, 4-aminophenylphosphorylcholine, used for the conjugate construction, was purchased from Biosearch Technologies.

The effect of PC-tuftsin on proteinuria was determined in a mouse model for lupus, specifically, female NZBXW/F1 mice that develop lupus on a genetic background. Proteinuria levels were measured using Multistix (Bayer Diagnostics). This type of measurement is typically used in the clinic for assessing manifestation of lupus nephritis. Lupus nephritis is an inflammation of the kidney caused by systemic lupus erythematosus (SLE).

The mice, from age of 14 weeks, received subcutaneously PC-tuftsin at the concentration of 50 µg/0.1 ml per mouse (treatment; n=10) or PBS (control; n=10), three times a week. Proteinuria was defined as having a protein level of above 100 mg/dl in the urine.

Figure 7:
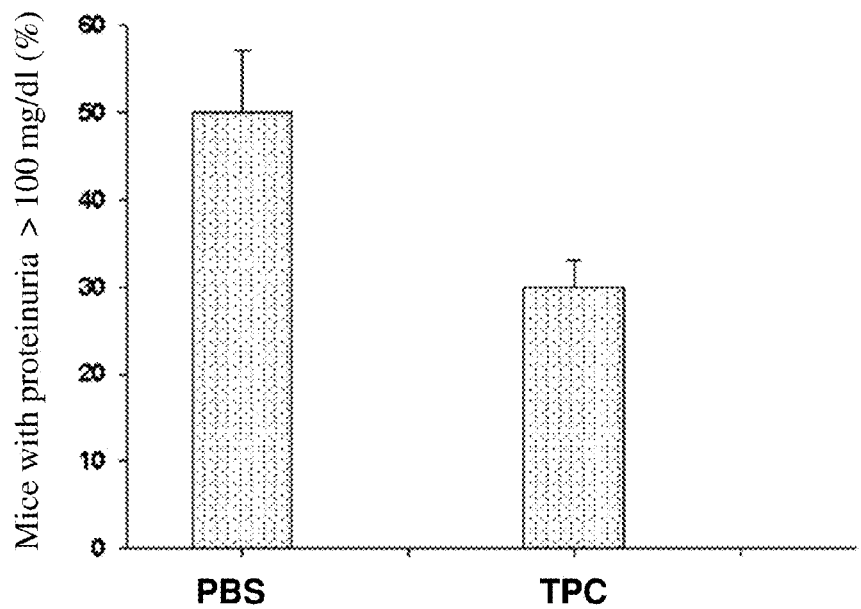
FIG. 7 shows the percentage of lupus mice with proteinuria (protein level above 100 mg/dl) treated with PC-tuftsin (TPC) or PBS (control), $p<0.02$.

The results demonstrate the inhibitory effect of PC-tuftsin treatment on the development of glomerulonephritis. As shown in FIG. 7, a significant attenuation (p<0.02) in proteinuria was exhibited in the group of mice treated with PC-tuftsin (TPC) in comparison with the control group, i.e. mice which received only the carrier (PBS).

Example 3: The Effect of PC-Tuftsin on the Morphology of Kidneys In Vivo

The effect of PC-tuftsin on the morphology of kidneys was determined in a lupus mouse model as in Examples 2. Kidney section obtained from kidneys of mice sacrificed after treatments were paraffin embedded. PAS staining was used to detect pathology of nephritis. Immunofluorescence staining was used for detecting immune complex deposits. The latter was implemented by incubating the paraffin embedded sections with FITC-conjugated-anti-mouse-IgG. Evaluation was performed by a pathologist.

Mice, from age of 14 weeks, received subcutaneously PC-tuftsin at the concentration of 50 µg/0.1 ml per mouse (treatment; n=10) or PBS (control; n=10), three times a week.

Figure 8A:
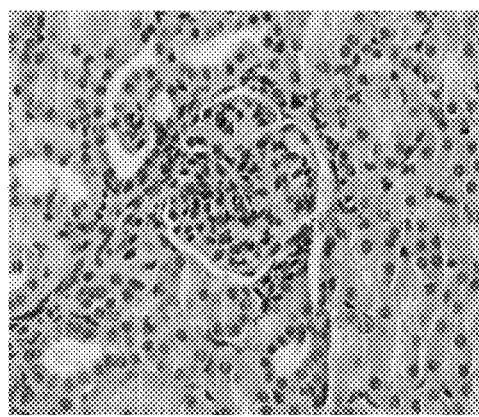
FIGS. 8A-8B show PAS stained kidney sections of lupus mice treated with PBS (control.
Figure 8B:
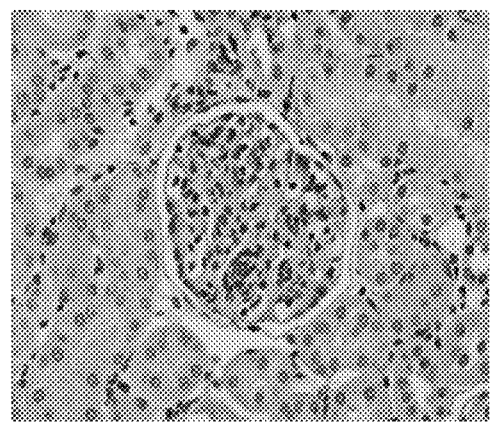

The results demonstrate a significant inhibitory effect of PC-tuftsin on the development of glomerulonephritis. Specifically, as illustrated in FIGS. 8A-8B, mice treated with PC-tuftsin did not display any pathology of nephritis, a normal glomeruli is exemplified (FIG. 8B; x60). Whereas the control group, i.e. mice which received only the carrier (PBS), presented a severe glomerulonephritis, strong destruction of the glomeruli, as well as infiltration of lymphocytes (FIG. 8A; x60).

Figure 9A:
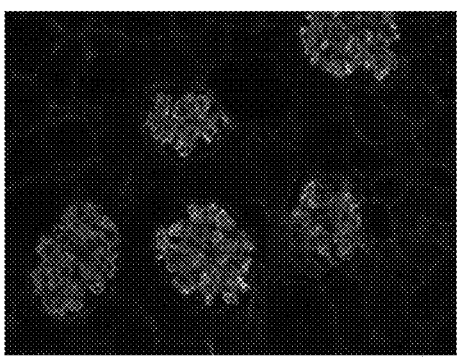
FIGS. 9A-9B show kidney sections of lupus mice treated with PBS (control.
Figure 9B:
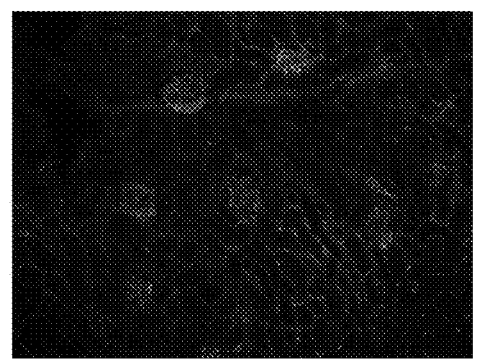

As shown in FIGS. 9A-9B, in lupus mice treated with PC-tuftsin, very mild immune complex deposits were exhibited in the glomeruli (FIG. 9B; x40) as compared to the control group (PBS), which present severe immune complex deposits (FIG. 9A; x20).

Example 4: The Effect of PC-Tuftsin on the Immune System In Vivo

The effect of PC-tuftsin on the immune system was determined in the lupus mouse model as in Examples 2. Cytokines analyses and T regulatory cell profiling were measured; these types of studies are typically used in the clinic for assessing manifestation of lupus nephritis.

Mice, from age of 14 weeks, received subcutaneously PC-tuftsin at the concentration of 50 fig/0.1 ml per mouse (treatment; n=10) or PBS (control; n=10), three times a week. In the cytokines studies, the relative mRNA expression levels of pro-inflammatory cytokine IFNγ and anti-inflammatory cytokine TGFβ were analyzed by real time RT-PCR using LightCycler (Roche). Total RNA was isolated from splenocytes and was reverse-transcribed into cDNA by using Moloney Murine Leukemia Virus Reverse Transcriptase (Promega). The resulting cDNA was subjected to real-time RT-PCR in the presence of specific primers, according to the manufacturer's instructions (Table 1). 20 µl reaction volume contained three mM $MgCl_2$, LightCycler HotStart DNA SYBR Green I mix (Roche), specific primer pairs, and five microliter of cDNA. The relative expression of IFNγ and TGFβ were normalized to β-actin levels.

TABLE 1

RT-PCR primers (forward and reverse respectively)

| Primer | Sequence (5' to 3') | SEQ. ID NO: |
|---|---|---|
| IFNγ | gaacgctacacactgc | 1 |
| IFNγ | ctggacctgtgggttg | 2 |
| IL-1β | ccccaactggtaaatca | 3 |
| IL-1β | ccgaggactaaggagtg | 4 |
| IL-10 | aacctcgtttgtacctct | 5 |
| IL-10 | caccatagcaaagggc | 6 |
| IL-17a | gggcaagggatgctctctag | 7 |
| IL-17a | ctgaagctgctgcagagctg | 8 |
| TNF-α | acgtcgtagcaaaccac | 9 |
| TNF-α | agatagcaaatcggctg | 10 |
| TGF-β | gaaccccattgctgt | 11 |
| TGF-β | gccctgtattccgtct | 12 |
| Foxp3 | taccacaatatgcgaccc | 13 |
| Foxp3 | ctcaaattcatctacggtcc | 14 |
| β-actin | gtgacgttgacatccg | 15 |
| β-actin | cagtaacagtccgcct | 16 |

Figure 10:
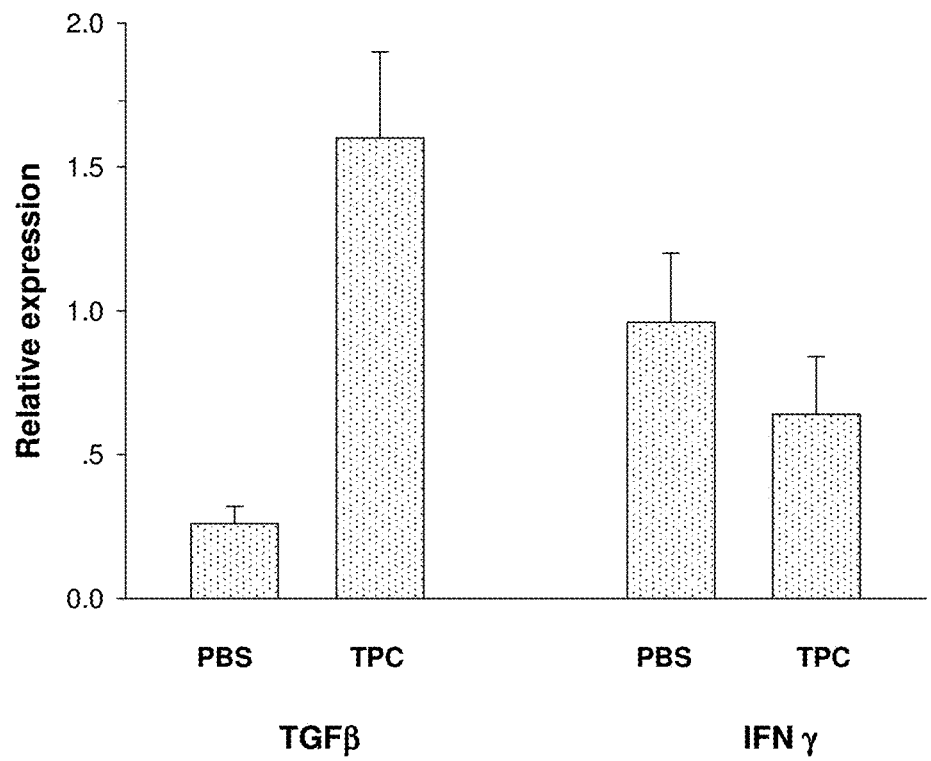
FIG. 10 shows relative mRNA expression levels of anti-inflammatory cytokine TGFβ ($p<0.001$) and pro-inflammatory cytokine IFNγ (p<0.03; relative to β-actin) in the splenocytes of lupus mice treated with PC-tuftsin (TPC) or PBS.

The results demonstrate that PC-tuftsin (TPC) exerts a significant inhibitory effect on the development of glomerulonephritis. As shown in FIG. 10, the splenocytes relative mRNA expression of anti-inflammatory cytokine TGFβ in mice treated with PC-tuftsin was significantly enhanced in comparison to the TGFβ mRNA derived from the PBS treated mice (p<0.001). In contrast, the splenocytes relative mRNA expression level of pro-inflammatory cytokine IFNγ in mice treated with PC-tuftsin (TPC) was significantly reduced, i.e. ameliorated in comparison to the IFNγ mRNA of the PBS control group (p<0.03). The results indicate that PC-tuftsin inhibited development of inflammation associated with nephritis.

Splenocytes protein level of anti-inflammatory cytokines TGFβ, and IL-10 and pro-inflammatory cytokines IFNγ, and IL-17 were quantified by DuoSet (R&D Systems), according to the manufacturer's instructions. Briefly, spleens from mice treated with PC-tuftsin or PBS were harvested, splenocytes were isolated ($5\times10^6$/ml) and incubated for 72 hours and thereafter assessed for contents of secreted cytokines.

Figure 11:
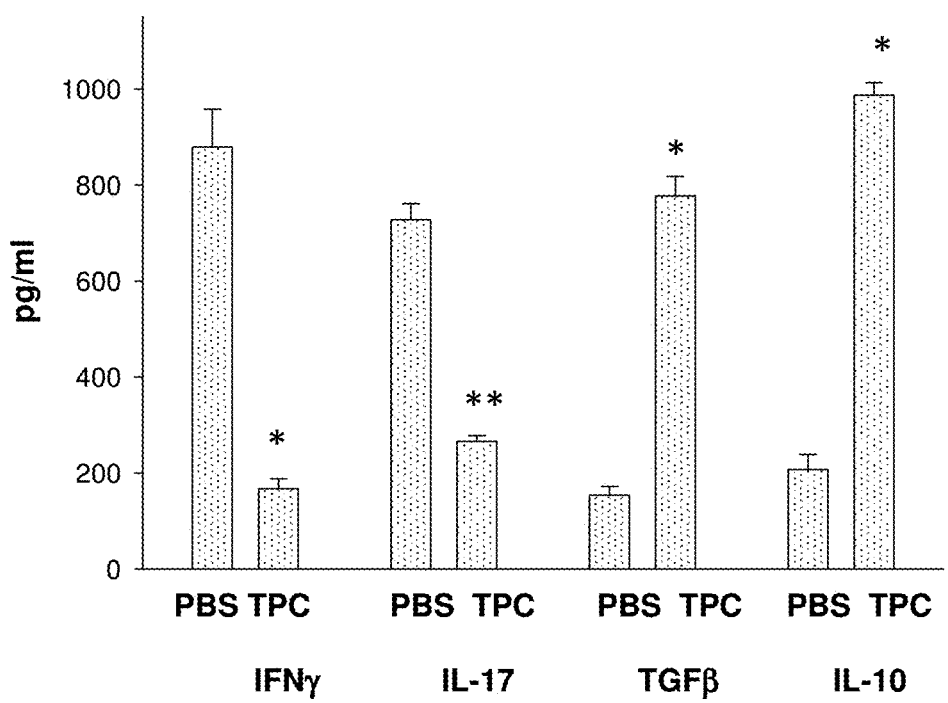
FIG. 11 shows protein level (in units of pg/ml) of anti-inflammatory cytokines TGFβ and IL-10 and pro-inflammatory cytokines IFNγ and IL-17 in the splenocytes of lupus mice treated with PC-tuftsin (TPC) or PBS (control).*=p<0.001, **=p<0.02.

The results demonstrate a significant inhibitory effect exerted by PC-tuftsin on the development of glomerulonephritis. As shown in FIG. 11, mice treated with PC-tuftsin (TPC) exhibited 5.1 and 4.8 increase in the protein levels of anti-inflammatory cytokines, TGFβ and IL-10, respectively, in comparison to PBS treatment (p<0.001). At the same time, the concentrations of pro-inflammatory cytokines IFNγ and IL-17 in PC-tuftsin (TPC) treated mice reduced by 5.2 and 2.7 fold, respectively as compared to control group (p<0.001, p<0.02, respectively). These results further indicate that PC-tuftsin treatment results with a significant inhibition of pro-inflammatory cytokines and enhanced expression of anti-inflammatory cytokines, thereby reduces, and even prevents, the occurrence of nephritis.

Finally, a T regulatory cell (Tregs) profiling assay was performed in isolated splenocytes incubated with the following antibodies: anti-CD4$^+$FITC, anti-CD25$^+$ APC and anti-FOXP3$^+$PE (eBioscience) and analyzed by FACS. Forward and side scatter gates adjusted to include all cells and to exclude debris (Becton Dickinson). Cells were gated on CD4+ cells, and for intracellular staining, the cells were incubated with a fixation solution, washed and resuspended in permeabilization solution (Serotec). Isotype control was used as reference.

Figure 12:
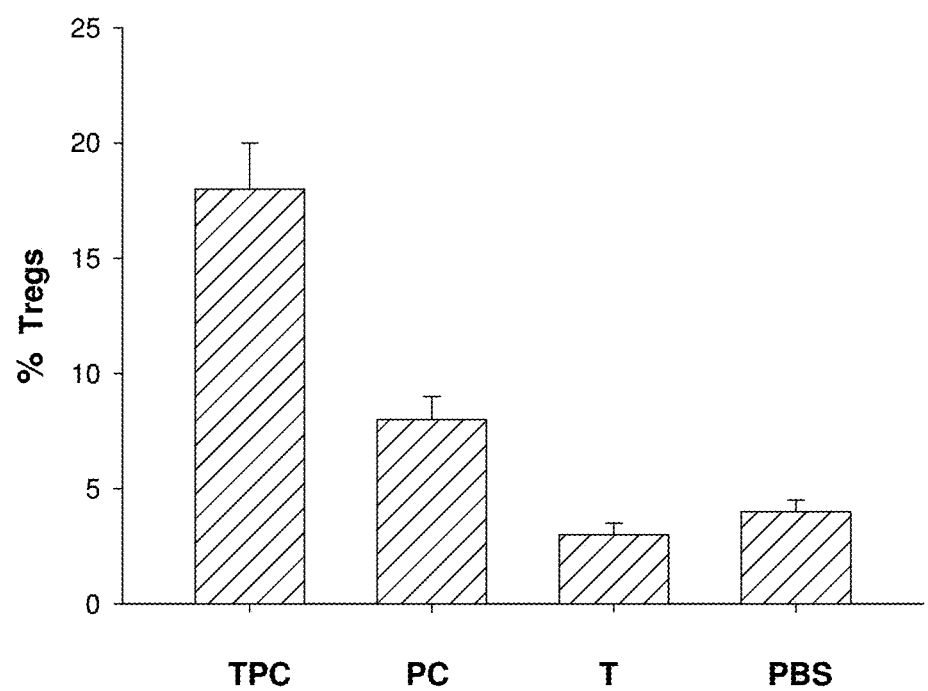
FIG. 12 shows FACS analysis of T regulatory cells levels (Tregs-CD4$^+$, CD25$^+$, FOXP3$^+$) in lupus mice treated with PC-tuftsin (TPC; p<0.02), phosphorylcholine (PC; p<0.01), tuftsin (T; p<0.01) or PBS (p<0.01).

Here too, the results demonstrate a significant inhibitory effect of PC-tuftsin treatment on the development of glomerulonephritis. As shown in FIG. 12 mice treated with PC-tuftsin (TPC) presented an enhancement of 18±2 percent in the Tregs, CD4$^+$CD25$^+$FOXP3$^+$ expression level (p<0.02), whereas with PBS treated mice an increase of only 4±0.6 percent was observed (p<0.01). Notably, phosphorylcholine (PC) or tuftsin (T) did not cause any significant elevation in Tregs level, (p<0.01). Moreover, the relative amount of Tregs obtained with PC-tuftsin is higher than the sum of relative Tregs obtained from each of PC and tuftsin. Thus, the PC-tuftsin exhibits a synergistic therapeutic effect.

Example 5: The Effect of PC-Tuftsin on Colitis Development In Vivo

The effect of PC-tuftsin on colitis development was determined in a mouse model subjected to induction of acute colitis by dextran sulfate sodium (DSS) treatment. Specifically, induction of colitis was carried out in male C57BL/6 mice ("colitis mice") by supplementing the drinking water (2.5% wt/v) for five days with DSS (mol. wt. 36,000-50,000).

Two groups of mice were fed daily via oral ingestion using a feeding-needle, with PC-tuftsin at a concentration of 500 μg/0.1 ml per mouse (treatment; n=10), or PBS (control; n=10). These compounds were given during 11 days starting two days before DSS administration. A third group of mice (n=10) were not induced with colitis, i.e. did not receive DSS, nor any treatment. All the mice groups had an identical average body weight (27-29 gr).

Figure 13A:
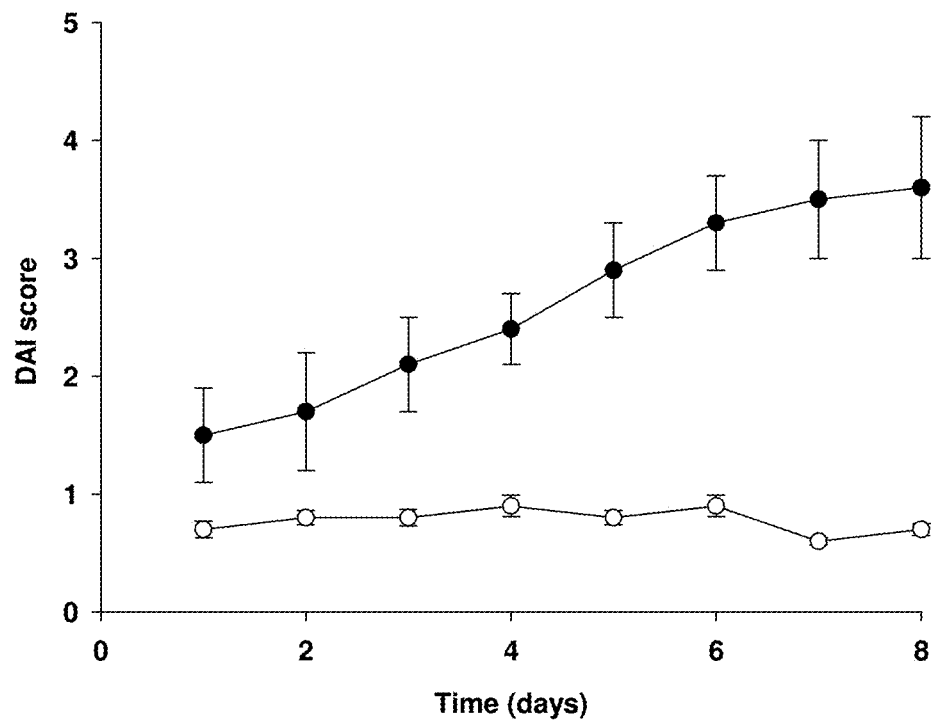
FIGS. 13A-13D show progression over time as a function of daily disease activity (DAI.

Assessment of colitis development was performed by monitoring body weight, rectal bleeding, stool consistency, and survival every second day. Intestinal bleeding was followed by Hemoccult test and observation of bleeding signs on the anus or gross bleeding. The daily disease activity index (DAI) was calculated by grading on a scale of zero to four the following parameters: change in weight (0, <1%; 1, 1-5%; 2, 5-10%; 3, 10-15%; and 4, >15%), intestinal bleeding (0, negative; 4, positive), and stool consistency (0, normal; 2, loose stools; 4, diarrhea). The combined scores were then divided by three to obtain the final disease activity index. Ten days following disease induction, mice were sacrificed and the large intestine was collected and evaluated for colon length and microscopic colonic damage. For microscopic scoring, the proximal, medial, and distal portions of the colon and the cecum were fixed in 10% phosphate-buffered formalin. Paraffin-embedded sections were stained with H&E. The degree of histological damage and inflammation was graded in a blinded fashion by an expert pathologist The results demonstrate an amelioration effect of PC-tuftsin on the development of DSS induced colitis. As shown in FIG. 13A, the DAI score of colitis mice treated with PC-tuftsin (empty circle) was around 0.9 (p<0.02) at the last day of the experiment, day 8, which was significantly lower than the DAI of the control group (PBS, solid circle). The latter gradually increased with time reaching the value of 2.6 after 5 days.

Figure 13B:
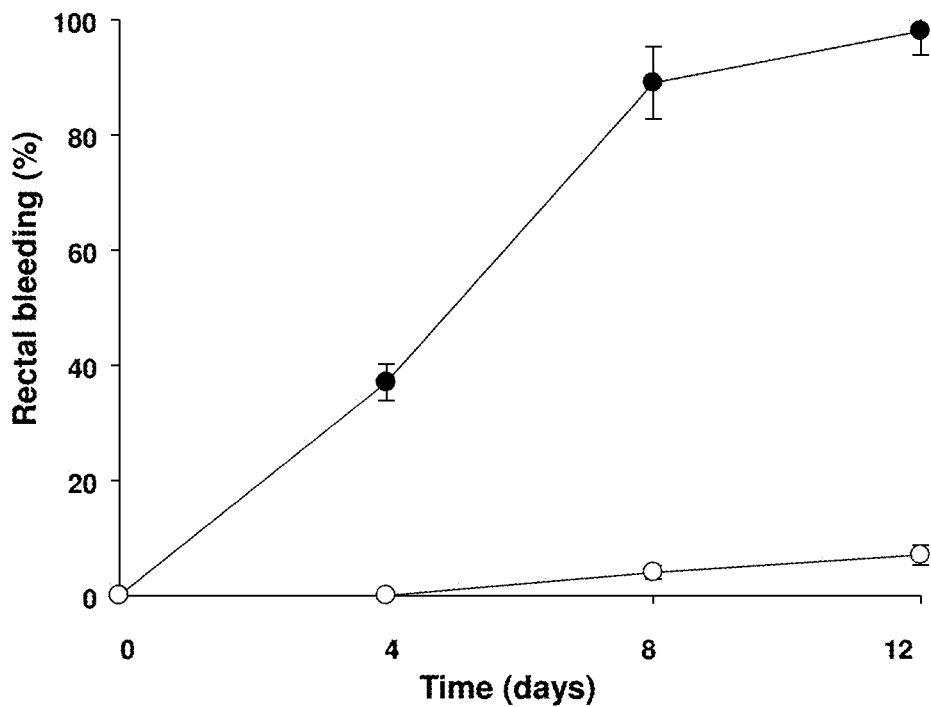
Figure 13C:
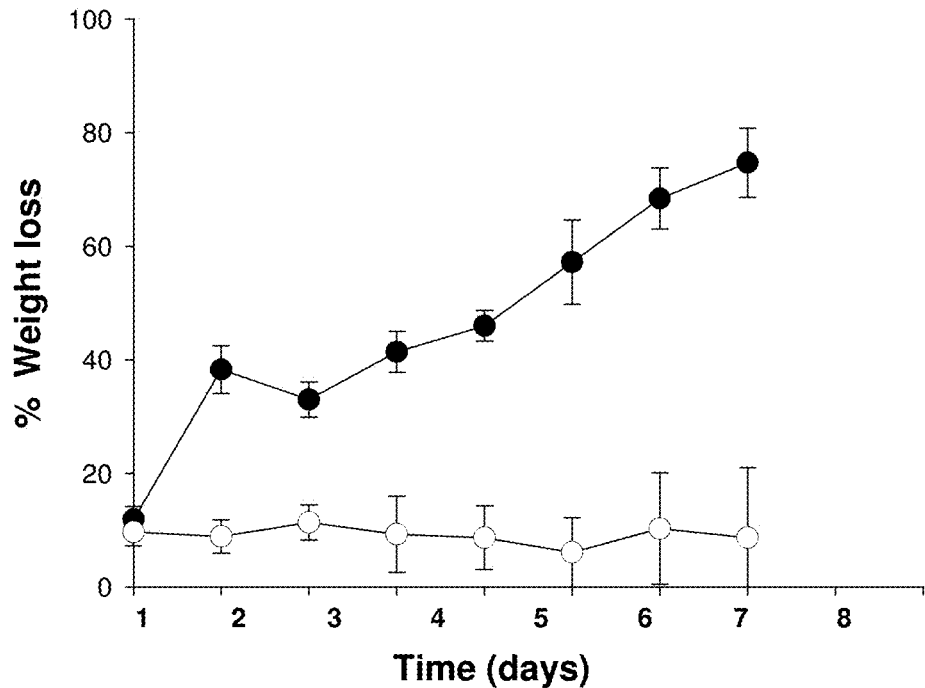
Figure 13D:
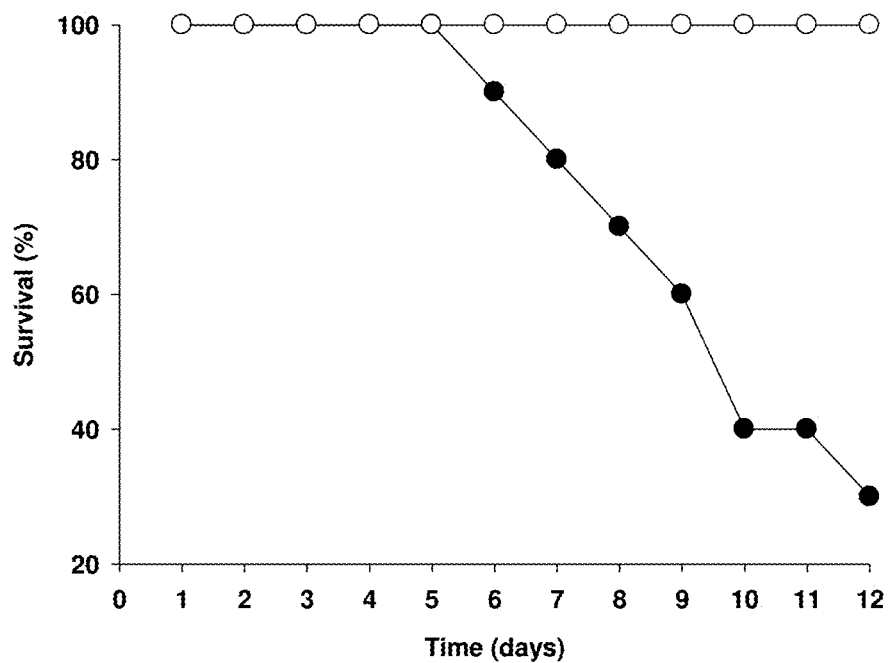

Furthermore, as illustrated in FIGS. 13B-13C, mice treated with PC-tuftsin (empty circle) exhibited significantly low rectal bleeding (13B; p<0.001) and loss of weight (13C; p<0.001) in comparison with the control (PBS treated, solid circle) mice. Finally, as illustrated in FIG. 13D, mice treated with PC-tuftsin (empty circle) exhibited significantly higher survival. After 5 days, a drop in the survival was exhibited with the PBS treated mice (solid circles), whereas 100% of the mice treated with PC-tuftsin (empty circle) were still alive, even after day 12.

Figure 14A:
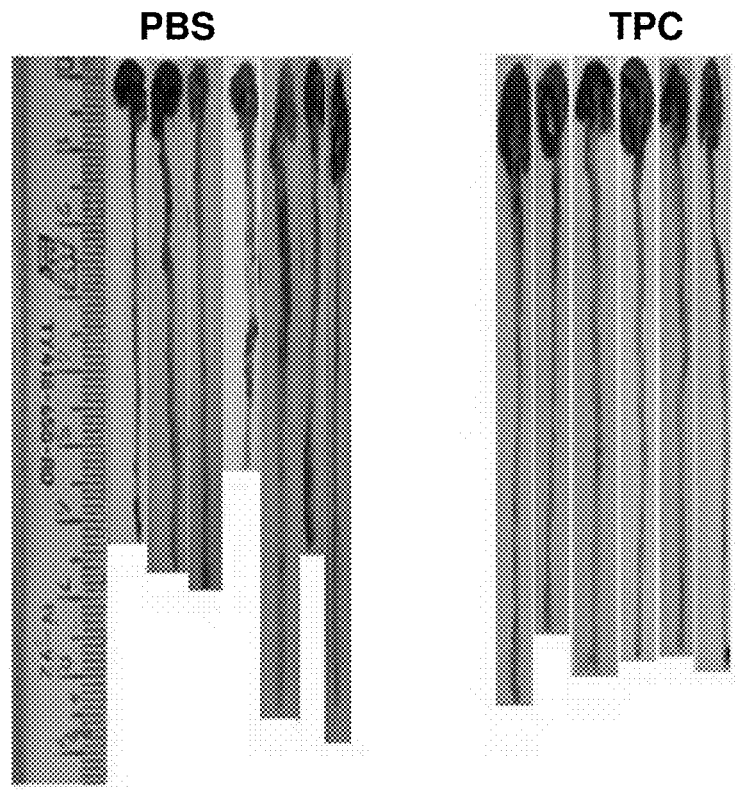
FIGS. 14A-14B show colons (FIG. 14A) and colon length analysis (FIG. 14B; p<0.02) in IBD mice following treatment with PC-tuftsin (TPC) or PBS.
Figure 14B:
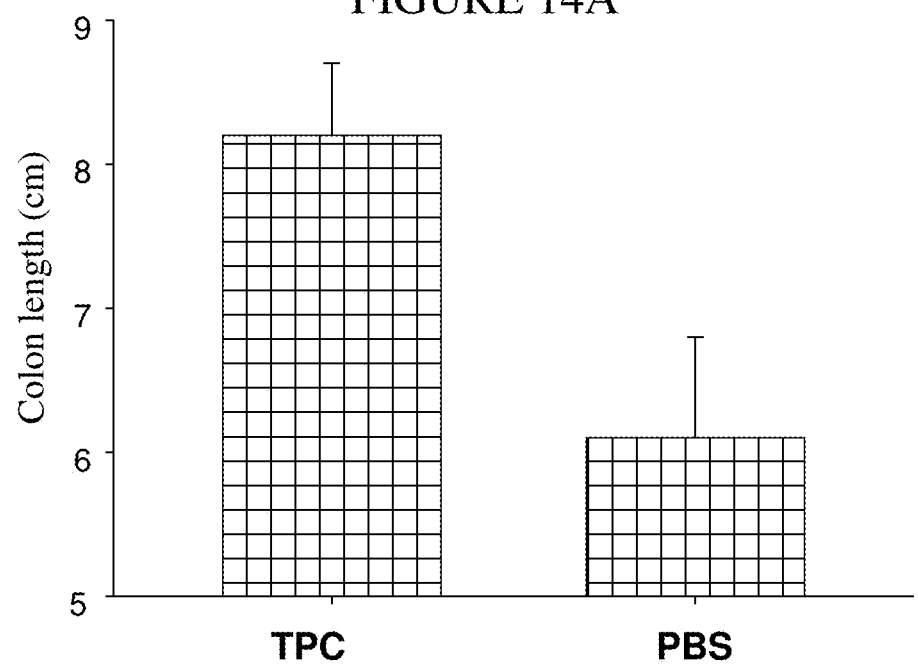

As exemplified in FIGS. 14A-14B, the colon length of mice treated with PC-tuftsin (TPC) was eight cm, in comparison with the control (PBS treated) mice, which shortened from eight cm to five-six cm (p<0.02).

Figure 15:
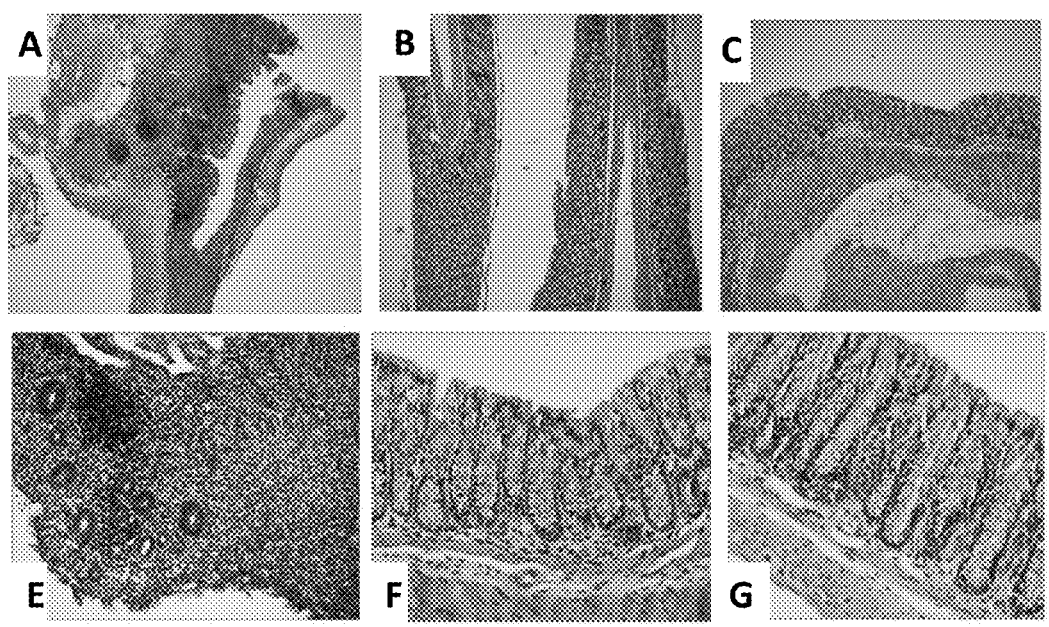
FIGS. 15A-15G show H&E stained colon sections of IBD mice treated with PBS (control.

Finally, as shown in FIGS. 15A-15G, histological analyses of colon section from the colons of all three mice groups revealed that PC-tuftsin treatment (FIGS. 15B; x20, 15F; x60) attenuated colon destruction as oppose to the control treatments, namely, PBS treatment (FIGS. 15A; x10, 15E; x40) and healthy mice, i.e. mice not subjected to DSS induction of colitis (FIGS. 15C; x20, 15G; x60). No difference was noted in the structure of the colon epithelia in healthy mice (FIGS. 15C, 15G) nor in colitis mice treated with PC-tuftsin (FIGS. 15B, 15F), whereas a strong infiltration of cells and zoom out of the glands were seen in colitis mice treated with PBS (FIGS. 15A, 15E).

Example 6: The Effect of PC-Conjugates on Collagen Induced Arthritis (CIA) In Vivo Previous studies showed that PC-OVA treatment of CIA mice, i.e. mice with collagen induced arthritis, resulted in amelioration of progression of inflammation associated with a shift from Th1 to Th2 response. In the current study the effect of PC-tuftsin, PC-glycan and MPC on disease progression in male DBA/1 mice with collagen induced arthritis is assessed.

For obtaining PC-Glycan, the PC or PC derivative is attached directly to a glycan moiety, such as Galβ1-4 [Fucα1-3]GlcNAc and to N-acetyl glucosamine to form PC-Galβ1-4[Fucα1-3]GlcNAc and PC—N-acetyl glucosamine (PC-GlcNAc), respectively.

Treatment of an animal model for arthritis with the PC-conjugates of the invention is performed according to two regimes: (1) Prophylactic (preventive) protocol, with collagen induced arthritis (CIA) mice in which the PC-conjugates are administered two days before induction of arthritis by injection of collagen-II; PC-conjugates are administered at the age of eight weeks before clinical manifestation of arthritis is detected; (2) Therapeutic protocol, where the PC-conjugates are administered when the disease is in the progression state (e.g. CIA at 20 weeks of age, which is similar to lupus at 24 weeks of age).

Male DBA/1 mice receive 50 μg of chick type II collagen (CII) in 1:1 emulsion with Freund's complete adjuvant at the base of the tail. Mice are evaluated by two blind observers three times a week, for signs of arthritis. Evaluation is based on the following severity scores: 0=normal, 1=erythema, 2=erythema plus swelling, 3=extension/loss of function, and total score=sum of four limbs. For the prophylactic protocol, mice are treated with PC-conjugates, 3 μg/0.1 ml per mouse subcutaneously on day −2, day 0 and day 21. For the therapeutic studies, mice are treated three times a week with PC-conjugates, 3 μg/0.1 ml PBS subcutaneously for 14 days commencing 1 day after CIA is clinically detectable. Control mice receive the carrier (PBS), or the moiety alone (e.g. tuftsin, polymer 2-methacryloyloxyethyl and glycan) at time points similar to those used for the PC-conjugates.

Proliferation is assessed as follows: Draining lymph node cells (DLN) and splenocytes are cultured at $2\times10^6$/ml for 96 hrs in RPMI-1640 medium, supplemented with 10% heat-inactivated fetal bovine serum, 2 mM L-glutamine, 1 mM sodium pyruvate, 0.1 mM non-essential amino acids, 100 U/ml penicillin, 100 µg/ml streptomycin and 50 µM 2-ME. The cells are labeled with Carboxyfluorescein succinimidyl ester (CFSE) and co-cultured with or without collagen-II (50 µg/ml) for 5 days. Then, lymphocytes are harvested, proliferation is assessed by the CFSE dilution method and flow cytometry, and presented as MFI (mean fluorescence intensity).

Cytokines' profile is assessed as follows: Culture fluids of splenocytes and DLN cells following exposure to collagen-II (50 µg/ml) or Concanavalin A (Con-A; 5 µg/ml) for 48 hrs and 72 hrs respectively, are harvested and stored at ca. −80° C. The effect of the PC-conjugates is examined by following Th1/Th2/Th17 selected cytokines. Specifically, the level of pro- and anti-inflammatory cytokines (IL-1, IL-2, IFNγ, IL-4, IL-10, IL-15, IL-17 and TNFα) is monitored using the MILLIPLEX MAP Mouse Cytokine kit (Millipore) according to the manufacturer's instructions, on Luminex (Bio-Plex®). TGFβ level is monitored by ELISA kit.

Based on the cytokine profile, selected cytokines are chosen for measurements of the mRNA level using quantitative real time RT-PCR, as detailed in Example 4. cDNA samples are amplified using specific primers (Table 1).

Autoantibodies expression level in the blood is evaluated as follows: blood is taken from the different groups of mice at different time points and the titers of anti-collagen-II and anti-PC in the sera are followed by ELISA. Briefly, the ELISA plates are coated with collagen-II (10 µg/ml), PC-KLH (10 µg/ml), glycan (10 µg/ml), tuftsin (10 µg/ml) or 2-methacryloyloxyethyl polymer (10 µg/ml) in PBS, overnight at 4° C. BSA (3% in PBS) blocked plates are then exposed to different dilutions of sera (1:200 till 1:10,000) for 2 hrs at room temperature. The binding is probed with anti-mouse IgG or IgM conjugated to alkaline phosphatase and appropriate substrate. The data are read at 405 nM ref. 600 nM. Anti-CCP (cyclic citrullinated peptide) antibodies titers are determined using the anti-DIASTAT anti-CCP2 following manufacturer's instructions with the following modifications: mouse sera is diluted to 1:10 or 1:100 in sample diluent, and the secondary antibody is substituted with alkaline phosphatase-conjugated goat anti-mouse IgG.

Histopathology of mice paws is also assessed as follows: mouse paw is fixed in 4% neutral buffered formalin (Sigma), decalcified, cut, and stained with H&E or with Nuclear Fast Rubine-Aniline Blue-Orange G. Four coronal sections 80 µm apart are scored by two independent observers, at low power for cellular infiltration, exudation, and pannus, and at low (610) and high (6100) power for bone erosion and cartilage destruction. A semi quantitative graded scale from 0 to 3 is used, as follows: 0, no changes; 1, mild changes; 2, moderate changes; and 3, most severe changes observed in the experiments. Cartilage destruction is determined as loss of cartilage in relation to the total cartilage area. A mean score for each animal is determined for each parameter, and the score is averaged to determine group means.

T regulatory evaluation is carried out as follows: $CD4^+$ $CD25^+$ Tregs can be induced during helminth infection. Splenocyte and DLN cells from mice in which CIA progression is attenuated upon treatment with a PC-conjugates are further analyzed for Th1/Th2/Th17 cytokine production and $CD4^+CD25^+$ $Foxp3^+$, T regulatory (Tregs) phenotype. The measurement of Tregs levels is performed by FACS using magnetic beads negative selection CD4+CD25+ Regulatory T Cell Isolation Kit. The kit contains a cocktail of lineage specific biotin-conjugated antibodies against CD8 (Ly-2), CD11b (Mac-1), CD45R (B220), CD49b (DX5), Ter-119, and anti-Biotin MicroBeads for depletion of non-CD4+ T cells, as well as CD25-PE and anti-PE MicroBeads for subsequent positive selection of CD4+CD25+ regulatory T cells. Cells are analyzed by flow cytometry. The mRNA level of Foxp3 is also analyzed by real-time RT-PCR as described above for the cytokines. The primer used include those listed in Table 1 above, among others.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A phosphorylcholine-conjugate comprising at least one phosphorylcholine moiety or a derivative thereof comprising phosphorylcholine covalently bound to at least one carrier, said carrier comprising an amino-acid sequence comprising SEQ ID NO: 17.

2. The phosphorylcholine-conjugate of claim 1, further comprising ES-62.

3. The phosphorylcholine-conjugate of claim 1, comprising one phosphorylcholine moiety or a derivative thereof comprising phosphorylcholine covalently bound to the at least one carrier.

4. The phosphorylcholine-conjugate of claim 1, comprising a plurality of phosphorylcholine moieties or derivatives thereof comprising phosphorylcholine covalently bound to the at least one carrier.

5. The phosphorylcholine-conjugate of claim 1, wherein the phosphorylcholine moiety or derivative thereof comprising phosphorylcholine and the at least one carrier are separated by a spacer.

6. A pharmaceutical composition comprising a phosphorylcholine-conjugate comprising at least one phosphorylcholine moiety or a derivative thereof comprising phosphorylcholine covalently bound to at least one carrier, said carrier comprising the amino-acid sequence set forth in SEQ ID NO: 17, and further comprising one or more pharmaceutically acceptable diluents or carriers.

7. The phosphorylcholine-conjugate of claim 1, wherein the derivative of phosphorylcholine comprising phosphorylcholine is selected from the group consisting of: 4-aminophenylphosphocholine, 4-diazoniophenylphosphorylcholine, 4-nitrophenylphosphocholine and 12-(3-Iodophenyl)-dodecylphosphocholine.

8. The phosphorylcholine-conjugate of claim 5, wherein the spacer is selected from amino acids and a polypeptide.

* * * * *

SEQUENCE LISTING

```
<160> NUMBER OF SEQ ID NOS: 22

<210> SEQ ID NO 1
<211> LENGTH: 16
<212> TYPE: DNA
<213> ORGANISM: Artificial Sequence
<220> FEATURE:
<223> OTHER INFORMATION: IFN-gamma primer

<400> SEQUENCE: 1
gaacgctaca cactgc                                                     16

<210> SEQ ID NO 2
<211> LENGTH: 16
<212> TYPE: DNA
<213> ORGANISM: Artificial Sequence
```

```
<220> FEATURE:
<223> OTHER INFORMATION: IFN-gamma primer

<400> SEQUENCE: 2
ctggacctgt gggttg                                                    16

<210> SEQ ID NO 3
<211> LENGTH: 17
<212> TYPE: DNA
<213> ORGANISM: Artificial Sequence
<220> FEATURE:
<223> OTHER INFORMATION: IL-1beta primer

<400> SEQUENCE: 3
ccccaactgg taaatca                                                   17

<210> SEQ ID NO 4
<211> LENGTH: 17
<212> TYPE: DNA
<213> ORGANISM: Artificial Sequence
<220> FEATURE:
<223> OTHER INFORMATION: IL-1beta primer

<400> SEQUENCE: 4
ccgaggacta aggagtg                                                   17

<210> SEQ ID NO 5
<211> LENGTH: 18
<212> TYPE: DNA
<213> ORGANISM: Artificial Sequence
<220> FEATURE:
<223> OTHER INFORMATION: IL-10 primer

<400> SEQUENCE: 5
aacctcgttt gtacctct                                                  18

<210> SEQ ID NO 6
<211> LENGTH: 16
<212> TYPE: DNA
<213> ORGANISM: Artificial Sequence
<220> FEATURE:
<223> OTHER INFORMATION: IL-10 primer

<400> SEQUENCE: 6
caccatagca aagggc                                                    16

<210> SEQ ID NO 7
<211> LENGTH: 20
<212> TYPE: DNA
<213> ORGANISM: Artificial Sequence
<220> FEATURE:
<223> OTHER INFORMATION: IL-17a primer

<400> SEQUENCE: 7
gggcaaggga tgctctctag                                                20

<210> SEQ ID NO 8
<211> LENGTH: 20
<212> TYPE: DNA
<213> ORGANISM: Artificial Sequence
<220> FEATURE:
<223> OTHER INFORMATION: IL-17a primer

<400> SEQUENCE: 8
ctgaagctgc tgcagagctg                                                20
```

```
<210> SEQ ID NO 9
<211> LENGTH: 17
<212> TYPE: DNA
<213> ORGANISM: Artificial Sequence
<220> FEATURE:
<223> OTHER INFORMATION: TNF-alpha primer

<400> SEQUENCE: 9
acgtcgtagc aaaccac                                                    17

<210> SEQ ID NO 10
<211> LENGTH: 17
<212> TYPE: DNA
<213> ORGANISM: Artificial Sequence
<220> FEATURE:
<223> OTHER INFORMATION: TNF-alpha primer

<400> SEQUENCE: 10
agatagcaaa tcggctg                                                    17

<210> SEQ ID NO 11
<211> LENGTH: 16
<212> TYPE: DNA
<213> ORGANISM: Artificial Sequence
<220> FEATURE:
<223> OTHER INFORMATION: TGF-beta primer

<400> SEQUENCE: 11 gaaccccat tgctgt                                                      16

<210> SEQ ID NO 12
<211> LENGTH: 16
<212> TYPE: DNA
<213> ORGANISM: Artificial Sequence
<220> FEATURE:
<223> OTHER INFORMATION: TGF-beta primer

<400> SEQUENCE: 12
gccctgtatt ccgtct                                                     16

<210> SEQ ID NO 13
<211> LENGTH: 18
<212> TYPE: DNA
<213> ORGANISM: Artificial Sequence
<220> FEATURE:
<223> OTHER INFORMATION: Foxp3 primer

<400> SEQUENCE: 13
taccacaata tgcgaccc                                                   18

<210> SEQ ID NO 14
<211> LENGTH: 20
<212> TYPE: DNA
<213> ORGANISM: Artificial Sequence
<220> FEATURE:
<223> OTHER INFORMATION: Foxp3 primer

<400> SEQUENCE: 14
ctcaaattca tctacggtcc                                                 20

<210> SEQ ID NO 15
<211> LENGTH: 16
<212> TYPE: DNA
<213> ORGANISM: Artificial Sequence
<220> FEATURE:
<223> OTHER INFORMATION: beta-actin
```

```
<400> SEQUENCE: 15
gtgacgttga catccg                                                    16

<210> SEQ ID NO 16
<211> LENGTH: 16
<212> TYPE: DNA
<213> ORGANISM: Artificial Sequence
<220> FEATURE:
<223> OTHER INFORMATION: beta-actin primer

<400> SEQUENCE: 16
cagtaacagt ccgcct                                                    16

<210> SEQ ID NO 17
<211> LENGTH: 4
<212> TYPE: PRT
<213> ORGANISM: Artificial Sequence
<220> FEATURE:
<223> OTHER INFORMATION: synthetic peptide

<400> SEQUENCE: 17

Thr Lys Pro Arg
1

<210> SEQ ID NO 18
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: X is absent or Arg.

<400> SEQUENCE: 18

Thr Lys Pro Xaa
1

<210> SEQ ID NO 19
<211> LENGTH: 5
<212> TYPE: PRT
<213> ORGANISM: Artificial Sequence
<220> FEATURE:
<223> OTHER INFORMATION: synthetic peptide

<400> SEQUENCE: 19

Thr Lys Pro Pro Arg
1               5

<210> SEQ ID NO 20
<211> LENGTH: 4
<212> TYPE: PRT
<213> ORGANISM: Artificial Sequence
<220> FEATURE:
<223> OTHER INFORMATION: synthetic peptide

<400> SEQUENCE: 20

Ser Lys Pro Arg
1

<210> SEQ ID NO 21
<211> LENGTH: 4
<212> TYPE: PRT
<213> ORGANISM: Artificial Sequence
<220> FEATURE:
```

```
<223> OTHER INFORMATION: synthetic peptide

<400> SEQUENCE: 21

Thr Arg Pro Arg
1

<210> SEQ ID NO 22
<211> LENGTH: 4
<212> TYPE: PRT
<213> ORGANISM: Artificial Sequence
<220> FEATURE:
<223> OTHER INFORMATION: synthetic peptide

<400> SEQUENCE: 22

Ser Lys Pro Lys
1
```